(12) United States Patent
Gupta et al.

(10) Patent No.: US 10,408,820 B2
(45) Date of Patent: Sep. 10, 2019

(54) COMPOUNDS FOR MODULATING INTEGRIN CD11B/CD18

(71) Applicant: The General Hospital Corporation, Boston, MA (US)

(72) Inventors: Vineet Gupta, Glenview, IL (US); M. Amin Arnaout, Chestnut Hill, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 262 days.

(21) Appl. No.: 14/311,069

(22) Filed: Jun. 20, 2014

(65) Prior Publication Data

US 2014/0303026 A1 Oct. 9, 2014

Related U.S. Application Data

(63) Continuation of application No. 13/614,046, filed on Sep. 13, 2012, now Pat. No. 8,846,667, which is a continuation of application No. 12/456,692, filed on Jun. 19, 2009, now Pat. No. 8,268,816, which is a continuation of application No. PCT/US2007/025878, filed on Dec. 18, 2007.

(60) Provisional application No. 60/875,728, filed on Dec. 19, 2006.

(51) Int. Cl.

| | |
|---|---|
| *G01N 33/50* | (2006.01) |
| *C07C 233/81* | (2006.01) |
| *C07C 251/20* | (2006.01) |
| *C07C 311/39* | (2006.01) |
| *C07D 213/85* | (2006.01) |
| *C07D 239/48* | (2006.01) |
| *C07D 249/10* | (2006.01) |
| *C07D 263/46* | (2006.01) |
| *C07D 265/34* | (2006.01) |
| *C07D 277/14* | (2006.01) |
| *C07D 277/36* | (2006.01) |
| *C07D 277/42* | (2006.01) |
| *C07D 277/54* | (2006.01) |
| *C07D 277/72* | (2006.01) |
| *C07D 311/16* | (2006.01) |
| *C07D 333/22* | (2006.01) |
| *C07D 333/68* | (2006.01) |
| *C07D 417/06* | (2006.01) |
| *C07D 417/12* | (2006.01) |
| *C07D 417/14* | (2006.01) |
| *C07D 471/04* | (2006.01) |
| *C07D 471/06* | (2006.01) |
| *C07D 498/04* | (2006.01) |
| *C07D 513/18* | (2006.01) |

(52) U.S. Cl.
CPC ....... *G01N 33/5032* (2013.01); *C07C 233/81* (2013.01); *C07C 251/20* (2013.01); *C07C 311/39* (2013.01); *C07D 213/85* (2013.01); *C07D 239/48* (2013.01); *C07D 249/10* (2013.01); *C07D 263/46* (2013.01); *C07D 265/34* (2013.01); *C07D 277/14* (2013.01); *C07D 277/36* (2013.01); *C07D 277/42* (2013.01); *C07D 277/54* (2013.01); *C07D 277/72* (2013.01); *C07D 311/16* (2013.01); *C07D 333/22* (2013.01); *C07D 333/68* (2013.01); *C07D 417/06* (2013.01); *C07D 417/12* (2013.01); *C07D 417/14* (2013.01); *C07D 471/04* (2013.01); *C07D 471/06* (2013.01); *C07D 498/04* (2013.01); *C07D 513/18* (2013.01); *C07C 2601/14* (2017.05)

(58) Field of Classification Search
CPC .................. G01N 33/5032; C07C 233/81; C07C 251/20; C07D 311/39; C07D 213/85
USPC ........................................................ 435/7.23
See application file for complete search history.

(56) References Cited

U.S. PATENT DOCUMENTS

| | | | |
|---|---|---|---|
| 6,251,395 B1 * | 6/2001 | Gallatin et al. ............ | 424/144.1 |
| 7,718,680 B2 | 5/2010 | Pellecchia et al. | |
| 2002/0052396 A1 | 5/2002 | Bailey et al. | |
| 2004/0002526 A1 | 1/2004 | Klein et al. | |

(Continued)

FOREIGN PATENT DOCUMENTS

| | | |
|---|---|---|
| FR | 2858324 A1 | 2/2005 |
| WO | 2000/010573 A1 | 3/2000 |

(Continued)

OTHER PUBLICATIONS

Xiong et al. (The J. of Immunology, 2003:171; 1042-1050) in view of Arnaout (2005/0227296) in view of Reyes et al. J Biomed Mater Res 67A: 328-333, 2003.*

(Continued)

*Primary Examiner* — Shirley V Gembeh

(57) ABSTRACT

The application describes an assay for the identification of small molecule modulators of integrin CD11b/CD18 and small molecules capable of modulating activity of this receptor. Such compounds may be used in certain embodiments for treating a disease or condition selected from inflammation, immune-related disorders, cancer, ischemia-reperfusion injury, stroke, neointimal thickening associated with vascular injury, bullous pemphigoid, neonatal obstructive nephropathy, and cardiovascular disease, or in other embodiments for the treatment of a disease or condition selected from immune deficiency, acquired immune deficiency syndrome (AIDS), myeloperoxidase deficiency, Wiskott-Aldrich syndrome, chronic granulomatous disease, hyper-IgM syndromes, leukocyte adhesion deficiency, Chediak-Higashi syndrome, and severe combined immunodeficiency.

14 Claims, 9 Drawing Sheets

(56) References Cited

U.S. PATENT DOCUMENTS

| | | | |
|---|---|---|---|
| 2004/0116468 A1 | 6/2004 | Nakagawa et al. | |
| 2005/0042213 A1 | 2/2005 | Gelder et al. | |
| 2005/0227296 A1* | 10/2005 | Arnaout | 435/7.2 |
| 2005/0282840 A1 | 12/2005 | Ross et al. | |
| 2006/0224234 A1 | 10/2006 | Jayaraman et al. | |
| 2007/0048216 A1 | 3/2007 | Norenberg et al. | |
| 2008/0033025 A1 | 2/2008 | Pellecchia et al. | |
| 2009/0069288 A1 | 3/2009 | Breinlinger et al. | |
| 2009/0130098 A1 | 5/2009 | Goodman et al. | |
| 2010/0056503 A1 | 3/2010 | Gupta et al. | |
| 2010/0331315 A1 | 12/2010 | Haddach et al. | |

FOREIGN PATENT DOCUMENTS

| | | |
|---|---|---|
| WO | 2004/093803 A2 | 11/2004 |
| WO | 2005/007118 A2 | 1/2005 |
| WO | 2005/016227 A2 | 2/2005 |
| WO | 2005/020990 A1 | 3/2005 |
| WO | 2005/041951 A2 | 5/2005 |
| WO | 2005/076695 A2 | 8/2005 |
| WO | 2006/024699 A1 | 3/2006 |
| WO | 2008/082537 | 7/2008 |

OTHER PUBLICATIONS

Reyes et al. J Biomed Mater Res 67A: 328-333, 2003.*
Ason et al. (Nucleic Acids Res. 2004; 32(10); e83; 1-6).*
Young et al. (Journal of Biomolecular Screening 10(4); 2005).*
Current Protocols in Cell Biology (2001).*
Bjorklund et al., "Stabilization of the Activated $\alpha_M\beta_2$ Integrin by a Small Molecule Inhibits Leukocyte Migration and Recruitment," Biochemistry, 2006, vol. 45, pp. 2862-2871.
Carter et al., PNAS (2001), 98(21), pp. 11879-11884.
Celik et al., "Agonist Leukadherin-1 Increases CD11b/CD18-Dependent Adhesion Via Membran Tethers," Biophysical Journal, 2013, vol. 105, pp. 2517-2527.
Faridi et al., "Identification of novel agonists of the integrin CD11b/CD18," Bioorganic & Medicinal Chemistry Letters, 2009, vol. 19, pp. 6902-6906, DOI: 10.1016/j.bmcl.2009.10.077.
Faridi et al., "Small molecule agonists of integrin CD11b/CD18 do not induce global conformational changes and are significantly better than activating antibodies in reducing vascular injury," Biochimica et Biophysica Acta 1830 (2013) pp. 3696-3710.
Forino et al., PNAS (2005) 102(27):9499-9504.
Gill et al., JOC 2005, 70(26):10726-10731.
Maiguel et al., "Small Molecule-Mediated Activation of the Integrin CD11b/CD18 Reduces Inflammatory Diseases," Science Signaling, 2011, vol. 4(189), ra57, DOI: 10.1126/scisignal.2001811.
Lee et al., Crystal Structure of the A domain from the alpha subunit of Integrin CR3 (CD11B/CD18), Cell, Feb. 1995; vol. 80, pp. 631-633.
Nathan et al., "Tumor necrosis factor and CE11/CD18 (beta2) integrins act syngeristically to lower cAMP in human neutrophils," J Cell Biology, 1990, vol. 111, pp. 2171-2181.
Park et al., "A Simple, No-Wash Cell Adhesion-Based High-Throughput Assay for the Discovery of Small-Molecule Regulators of the Integrin CD11b/CD18," Journal of Biomolecular Screening, 2007, vol. 12, pp. 406, DOI: 10.1177/1087057106299162.
Reed et al., "Complement Receptor 3 Influences Toll-like Receptor 7/8-Dependent Inflammation," Journal of Biological Chemistry, 2013, vol. 288(13), pp. 9077-9083.
Shah, "Inflammation, Neointimal Hyperplasia, and Restenosis: As the Leukocytes Roll, the Arteries Thicken," Circulation, 2003, vol. 107(17), pp. 2175-2177, DOI: 10.1161/01.cir.0000069943.41206.bd.
Tautz et al., J. Biological Chemistry, 2005, 280(10):9400-9408.
Verma et al., Molecular Pharmaceuticals, 2008, 5(5):745-759.
Chemical Abstracts RN 344897-95-6; entered STN Jul. 8, 2001, 1 page.
ChemBridge Catalog # 5679982 4-{5-[(Z)-(3-Benzyl-4-oxo-2-thioxo-1,3-thiazolidin-5-ylidene)nriethyl]-2-furyl}benzoic acid, http//:www.hit2lead.com/result.asp?search=14662037, retrieved on Jan. 7, 2014.
ChemBridge Catalog # 5578913 4-{5-[(Z)-(2,4-Dioxo-3-phenyl-1,3-thiazolidin-5-ylidene)methyl]-2-furyl}benzoic acid, http//:www.hit2lead.com/result.asp?search=82461052, retrieved on Jan. 7, 2014.
ChemBridge Catalog # 6789780 Ethyl [(5Z)-5-{[5-(2,4-dichlorophenyl)-2-furyl]methylene}-2,4-dioxo-1,3-thiazolidin-3-yl]acetate, http//:www.hit2lead.com/result.asp?search=13199976, retrieved on Jan. 8, 2014.
ChemBridge Catalog # 6528335 2-Chloro-5-(5-{(Z)-[3-(4-fluorobenzyl)-2,4-dioxo-1,3-thiazolidin-5-ylidene]methyl}-2-furyl)benzoic acid, http//:www.hit2lead.com/result.asp?search=30881677, retrieved on Jan. 8, 2014.
ChemBridge Catalog # 6725132 Ethyl {(5Z)-2,4-dioxo-5-[(5-phenyl-2-furyl)methylene]-1,3-thiazolidin-3-yl}acetate, http//:www.hit2lead.com/result.asp?search=85021953, retrieved on Jan. 8, 2014.
ChemBridge Catalog #: 7476685 (5Z)-3-(2-Furylmethyl)-5-[(5-phenyl-2-furyl)methylene]-2-thioxo-1,3-thiazolidin-4-one, http//:www.hit2lead.com/result.asp?search=17650479, retrieved on Jan. 8, 2014.
EP Application No. 11 80 3961, Supplementary European Search Report, Date of completion Oct. 16, 2013, 1 page.
PCT Application No. PCT/US2011/034753, International Search Report, dated Oct. 3, 2011, 3 pages.
U.S. Appl. No. 12/456,692, Notice of Allowance, dated May 17, 2012.
U.S. Appl. No. 12/456,692, Final Office Action, dated Jan. 19, 2012.
U.S. Appl. No. 12/456,692, Office Action, dated Oct. 5, 2011.
U.S. Appl. No. 12/456,692, Final Office Action, dated Jul. 27, 2011.
U.S. Appl. No. 12/456,692, Office Action, dated Apr. 4, 2011.
U.S. Appl. No. 12/456,692, Office Action, dated Sep. 7, 2010.
U.S. Appl. No. 13/614,046, Office Action, dated Aug. 20, 2013.
U.S. Appl. No. 13/614,046, Notice of Allowance, dated Mar. 29, 2014.

\* cited by examiner

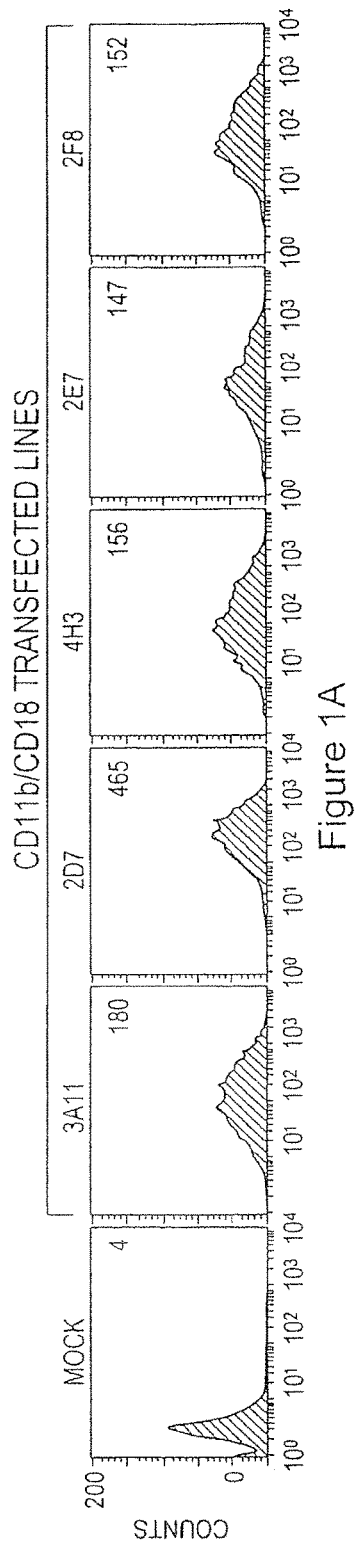
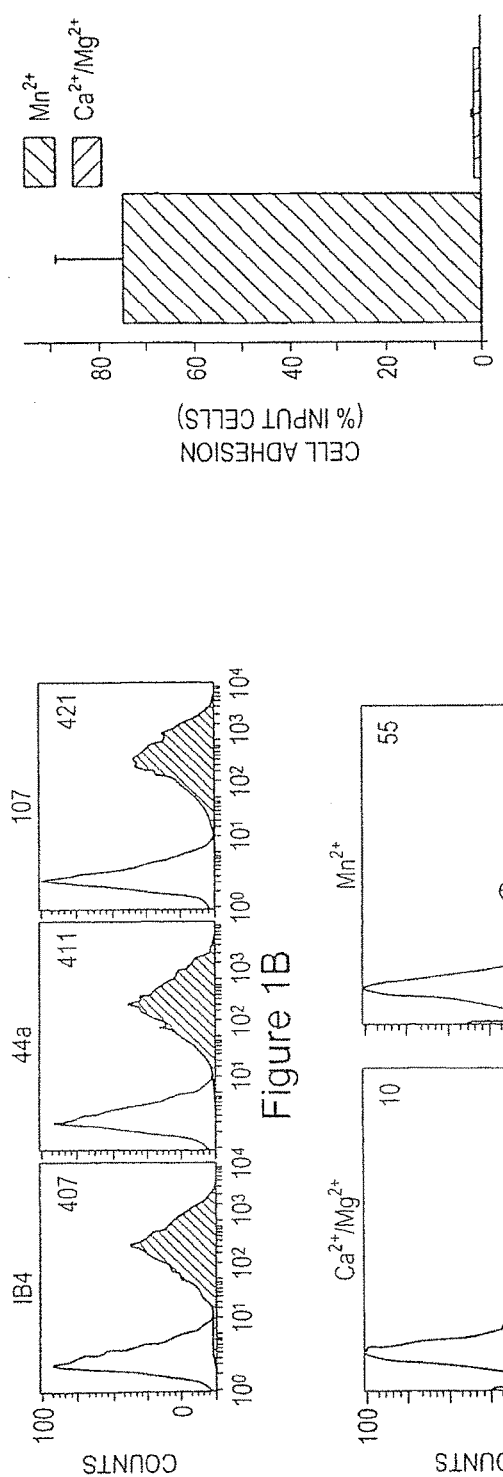
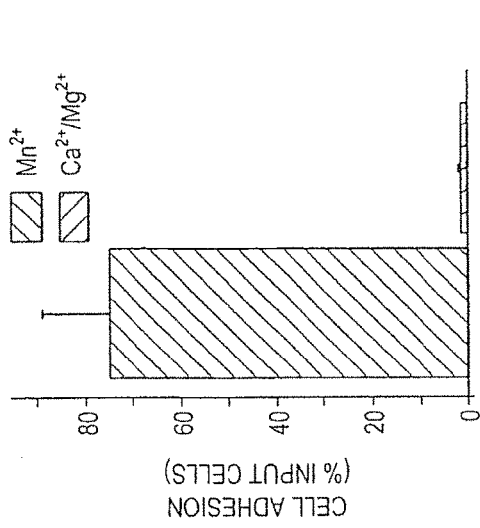

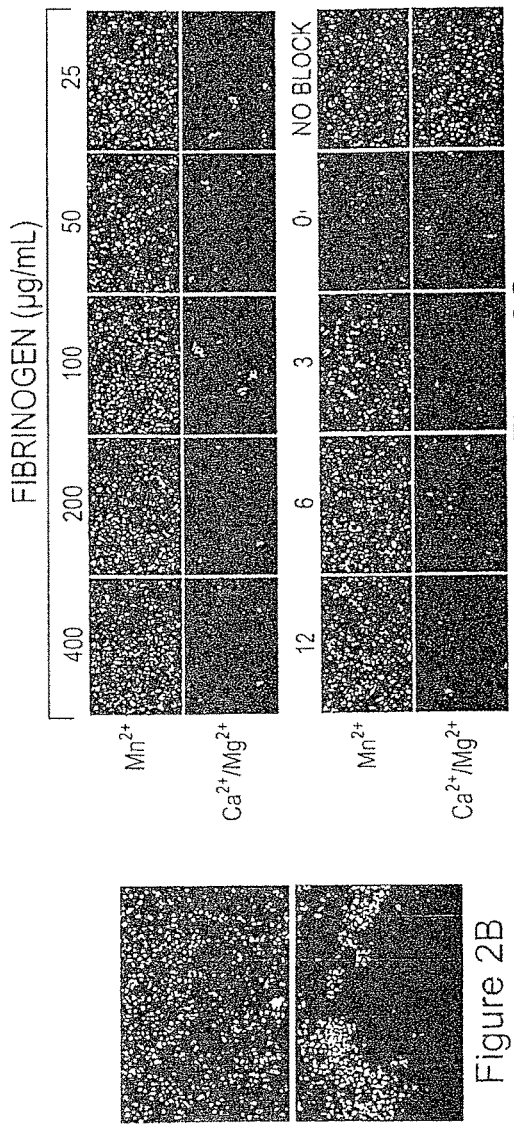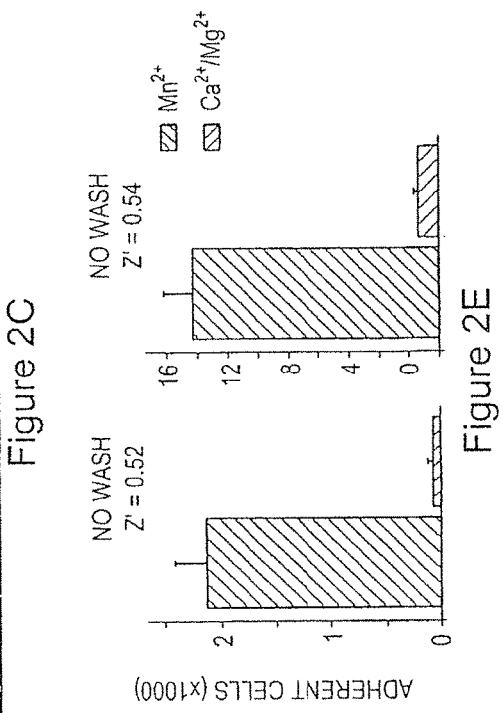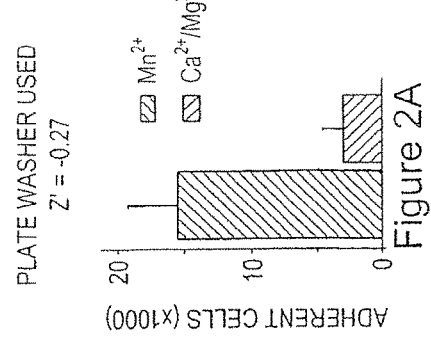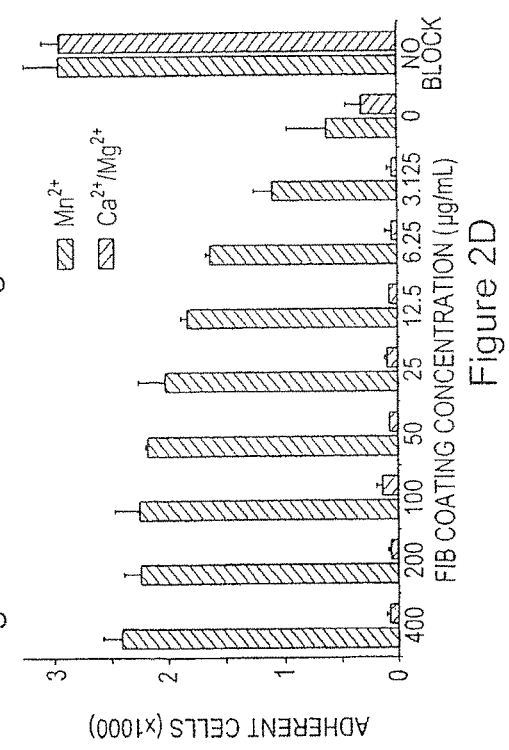
Figure 2A Figure 2B Figure 2C Figure 2D Figure 2E

COMPOUNDS FOR MODULATING INTEGRIN CD11B/CD18

CROSS-REFERENCES TO RELATED APPLICATIONS

This application is a Continuation of U.S. patent application Ser. No. 13/614,046, filed Sep. 13, 2012, which is a Division of U.S. patent application Ser. No. 12/456,692, filed Jun. 19, 2009 (now U.S. Pat. No. 8,268,816, issued Sep. 18, 2012), which is a Continuation of International Patent Application No. PCT/US2007/025878, filed Dec. 18, 2007, which claims the benefit of priority from U.S. Provisional Patent Application No. 60/875,728, filed Dec. 19, 2006, the contents of which applications are incorporated herein by reference in their entirety for all purposes.

STATEMENT REGARDING FEDERALLY SPONSORED RESEARCH OR DEVELOPMENT

This invention was made with government support under Grant Nos. 1R03NS053659 and K01 DK068253 awarded by the National Institutes of Health. The United States Government has certain rights in this invention.

BACKGROUND OF THE INVENTION

Integrins are non-covalently linked $\alpha/\beta$ heterodimeric receptors that mediate cell adhesion, migration and signaling. Together with their ligands, integrins play central roles in many processes including development, hemostasis, inflammation and immunity, and in pathologic conditions such as cancer invasion and cardiovascular disease. The $\beta 2$ integrins, which have a common $\beta$-subunit ($\beta 2$, CD18) but distinct $\alpha$-subunits (CD11a, CD11b, CD11c and CD11d), are critical leukocyte receptors that are important not only for the function of leukocytes but also the development of the inflammatory response in vivo. Leukocytes normally circulate in the vasculature in a quiescent state, but in response to inflammatory stimuli, adhere, transmigrate across the vascular endothelium, and enter areas of tissue inflammation where they participate in the destruction and removal of infectious agents and in amplifying the process of inflammation. The integrin CD11b/CD18 (complement receptor type 3 (CR3), Mac-1 or $\alpha M\beta 2$) is the predominant $\beta 2$ integrin receptor in neutrophils, macrophages and monocytes and mediates a large number of pro-inflammatory functions in these cells. CD11b/CD18 recognizes a wide variety of ligands, including the complement fragment iC3b, fibrinogen, blood-clotting factor X, CD54 (ICAM-1), the hookworm neutrophil inhibitory factor (NIF), and denatured proteins such as bovine serum albumin (BSA). Studies in CD11b−/− mice have shown that this integrin has a distinct and cooperative role (with integrin CD11a) in the inflammatory process. In addition to the knockout mice studies, the biological importance of this integrin in maintaining immunological homeostasis has also been illustrated by different pathological conditions where integrins are absent or defective—loss of functional $\beta 2$ integrins causes life-threatening infections in humans and mutations result in leukocyte adhesion deficiency type 1, where circulating neutrophils fail to adhere to or migrate across the endothelium and the patients are susceptible to recurrent, life-threatening bacterial infections. Similarly, improper excessive activation of leukocyte integrins is also harmful, as over-activation of $\beta 2$ integrins contributes to sustained inflammation, ischemia-reperfusion injury (including acute renal failure, atherosclerosis and autoimmune disorders, tissue damage) and the development of various autoimmune diseases. CD11b/CD18 is also implicated in stroke, neointimal thickening in response to vascular injury2, bullous pemphigoid, and neonatal obstructive nephropathy. Thus, there is a considerable potential for agents that block the binding of CD11b/CD18 to its physiologic ligands as therapeutics for the treatment of such inflammatory conditions.

Physiologic ligand binding by CD11b/CD is divalent-cation dependent and is mediated by CD11b von Willebrand factor type A (VWFA) domain, CD11bA-domain (A-domain). Blocking anti-CD11b/CD18 antibodies decreases ischemia/reperfusion injury, the area of myocardial infarction and liver cell injuries, and diminishes neointimal thickening and restenosis after balloon injury of carotid arteries in animal models. These antibodies are also effective in the treatment of endotoxic challenge and hemorrhagic shock and autoimmune injury in various organs including the kidney. However, antibody therapy is not ideal because adverse effects due to nonselective blockade of various other leukocyte functions may lead to severe complications. Similarly, neutrophil inhibitory factor (NIF), a 41-kDa glycoprotein ligand-mimic, is effective in attenuating the deleterious effects of excessive neutrophil activation in animal models, but its large size and immunogenicity preclude its use as a therapeutic agent. Additionally, although blockade of the binding sites of integrins with ligand-mimetic peptides or small molecules has proven effective in inhibiting the activities of $\beta 1$ and $\beta 3$ integrins, peptides derived either from CD11b/CD18 ligands or anti-CD11b/CD18 antibodies were not very efficacious in blocking ligand binding in vitro. The failure of these ligand-mimetic peptides to block the interaction between iC3b and CD11b/CD18 may be due to their improper conformation in solution or to the size of the ligand binding sites, which may be too extensive to block with a small peptide.

Current assays for the identification of regulators of CD11b/CD18 rely on purified proteins adsorbed to microtiter plates. Even though these assays are compatible with high-throughput screening (HTS), purification of the requisite amount of CD11b/CD18 from mammalian cells for a HTS campaign can be exceedingly difficult and the natural conformation of integrin may not be retained upon adsorption to the plastic surfaces. Optimized cell-based phenotypic assays that can be readily utilized in an HTS environment for the rapid identification of small molecule regulators of this important integrin are currently lacking. Recent reports also suggest that CD11b/CD18 has a central role in the resolution of inflammatory processes by modulating the egress of adherent neutrophils from the site of inflammation. This suggests that small molecule agonists of CD11b/CD18 may also have a role in treatment of certain inflammatory and other conditions. Here again, simple cell-based phenotypic assays for ready HTS adaptation are currently lacking.

Therefore what is needed are small molecules that selectively modulate CD11b/CD18 ligand binding, especially by targeting allosteric regulatory sites, such as the hydrophobic site-for-isoleucine (SILEN) pocket in CD11b/CD1824, which may prove to be a more promising therapeutic strategy. An effective assay for the rapid identification of small molecule modulators of integrin CD11b/CD18 is also needed.

SUMMARY OF THE INVENTION

One aspect of the invention relates to a compound of Formula (I)

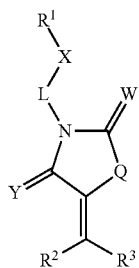

wherein

L is absent or is alkyl;

Q, W, and Y are independently selected from O and S;

X is absent or is selected from O, S, and NR⁴;

R¹ is selected from hydrogen, acyl, alkyl, alkenyl, alkynyl, aryl, heteroaryl, carbocyclyl, heterocyclyl, alkoxycarbonyl, alkylaminocarbonyl, alkylthiocarbonyl, sulfonate, sulfone, sulfoxide, and sulfonamide;

one of $R^2$ and $R^3$ is selected from alkyl, hydroxyalkyl, aminoalkyl, thioalkyl, alkoxyalkyl, aryl, aralkyl, heteroaryl, heteroaralkyl, carbocyclyl, carbocyclylalkyl, heterocyclyl, and heterocyclylalkyl;

the other of $R^2$ and $R^3$ is selected from hydrogen and alkyl; and

R⁴ is selected from hydrogen and alkyl.

One aspect of the invention relates to a compound of Formula (II)

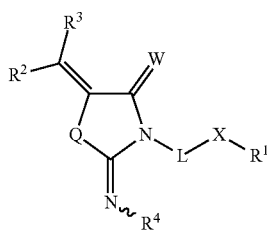

wherein

L is absent or is alkyl;

Q and W are independently selected from O and S;

X is absent or is selected from O, S, and NR⁵;

R¹ is selected from hydrogen, acyl, alkyl, alkenyl, alkynyl, aryl, heteroaryl, carbocyclyl, heterocyclyl, alkoxycarbonyl, alkylaminocarbonyl, alkylthiocarbonyl, sulfonate, sulfone, sulfoxide, and sulfonamide;

one of $R^2$ and $R^3$ is selected from alkyl, hydroxyalkyl, aminoalkyl, thioalkyl, alkoxyalkyl, aryl, aralkyl, heteroaryl, heteroaralkyl, carbocyclyl, carbocycloalkyl, heterocyclyl, and heterocycloalkyl;

the other of $R^2$ and $R^3$ is selected from hydrogen and alkyl; and

R⁴ and R⁵ are independently selected from hydrogen and alkyl;

provided that at least one of $R^2$ and $R^3$ is other than hydrogen.

One aspect of the invention relates to a compound of Formula (III)

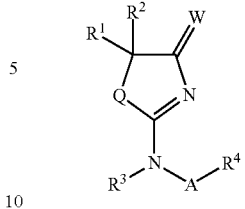

wherein

A is absent or is selected from C=O, C=S, and SO₂;

Q and W are independently selected from O and S;

R¹ and R² are independently selected from hydrogen, alkyl, alkoxy, alkoxyalkyl, hydroxyalkyl, aminoalkyl, thioalkyl, aralkyl, heteroaralkyl, carbocycloalkyl, and heterocycloalkyl;

R³ is selected from hydrogen and alkyl; and

R⁴ is selected from alkyl, aralkyl, heteroaralkyl, carbocycloalkyl, heterocycloalkyl, aryl, heteroaryl, carbocyclyl, and heterocyclyl.

One aspect of the invention relates to a compound of Formula (IV)

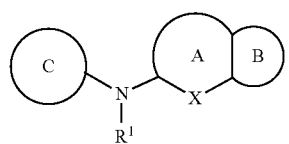

wherein

A and B are independently 5- or 6-membered ring selected from aryl, carbocycle, heterocycle, and heteroaryl, wherein A and B together form a fused bicyclic ring system;

C is a 5- or 6-membered ring selected from aryl, carbocycle, heterocycle, and heteroaryl;

X is selected from C(R²)(R³), N(R⁴), S, and O;

Z is selected from O, S, and NR⁵;

R¹ is selected from hydrogen, alkyl, and aralkyl;

R² is selected from hydrogen, alkyl, alkoxy, alkoxyalkyl, amino, aminoalkyl, hydroxy, hydroxyalkyl, thiol, and thioalkyl; or R¹ and R² together are C₁₋₃alkyl or —C₁₋₂alkyl-Z, thereby forming a 5- to 6-membered ring that is fused to A;

R³ is absent or is selected from hydrogen, alkyl, alkoxy, alkoxyalkyl, amino, aminoalkyl, hydroxy, hydroxyalkyl, thiol, and thioalkyl; or R⁴ is absent or is selected from hydrogen, alkyl, aryl, aralky, heteroaryl, heteroaralkyl, carbocyclyl, carbocycloalkyl, heterocyclyl, and heterocycloalkyl; and R⁵ is selected from hydrogen, alkyl, aryl, aralky, heteroaryl, heteroaralkyl, carbocyclyl, carbocycloalkyl, heterocyclyl, and heterocycloalkyl.

In certain embodiments, the invention relates to methods for the modulation of integrin CD11b/CD18 comprising administering a compound of the invention.

In certain embodiments, the invention relates to a pharmaceutical composition comprising a compound of the invention and a pharmaceutically acceptable diluent or carrier.

In certain embodiments, the invention relates to methods for treating a disease or condition selected from inflammation, immune-related disorders, cancer, ischemia-reperfusion injury, stroke, neointimal thickening associated with vascular injury, bullous pemphigoid, neonatal obstructive nephropathy, and cardiovascular disease, comprising administering a compound of the invention.

In certain embodiments, the invention relates to an assay for the identification of small molecule modulators of integrin CD11b/CD18.

In certain embodiments, the invention relates to the use of the described compounds in identification of sites and domains in integrin CD11b/CD18 and in integrin CD11a/CD18 that modulate activity of integrin CD11b/CD18 and in determining exact three-dimensional structure of the binding pocket, which can be used to derive more selective and/or potent binders. For example, a complex of CD11b/CD18 with a binding compound can be prepared and analyzed, e.g., by x-ray crystallography, nuclear magnetic resonance, or other suitable means, to identify the binding site of CD11b/CD18 that interacts with the compound.

In certain embodiments, computer-based modeling algorithms can be used to analyze the structures and conformations compounds that bind CD11b/CD18 to identify structural features that contribute to successful binding. In certain embodiments, such information is analyzed in conjunction with information about the structure or conformation of CD11b/CD18 or a binding pocket thereof, such as structural information obtained by analysis of CD11b/CD18 using analytical techniques such as x-ray crystallography or nuclear magnetic resonance, to analyze interactions between binding compounds and the binding pocket they interact with. Such analysis can be used to predict the portion of CD11b/CD18 that interacts with the compound, to select compounds that possess structural features correlated with desired binding activity from a library of test compounds, or to design structures that are expected to exhibit binding with CD11b/CD18 for testing in vivo or in vitro using assays as described herein.

BRIEF DESCRIPTION OF THE FIGURES

FIG. 1a shows surface expression profiling of various stable lines generated that express different levels of wild-type CD11b/CD18. FACS histograms showing cells stained with the heterodimer-specific mAb IB4. Mean fluorescence intensity (MFI) for mAb IB4 staining is shown in each panel.

FIG. 1b shows surface expression profiling of one clone (3F9) expressing wild-type CD11b/CD18 at high levels using three different mAbs. Mean fluorescence intensity (MFI) for mAb staining is shown in each panel.

FIG. 1c shows FACS analysis of the reactivity of conformation-sensitive mAb24. MFI values for mAb staining (filled histogram) are shown in each panel. No binding was observed with isotype control mAb (non-filled histogram).

FIG. 1d shows a bar graph showing the percent input cells (50,000 per well) adhering to the bottom of fibrinogen-coated wells in the presence of Ca2+ and Mg2+ (1 mM of each) or of 1 mM Mn2+ and quantitated by the measurement of cellular ATP levels from a 96-well plate adhesion assay performed using manual washing of the plate. Each bar represents mean+SD of triplicate determinations from a representative experiment.

FIG. 2a shows a bar graph showing the number of cells adhering to the bottom of fibrinogen-coated wells in the presence of Ca2+ and Mg2+ (1 mM of each) or of 1 mM Mn2+ and quantitated by measurement of cellular ATP levels from a 384-well plate adhesion assay performed using automated washing of the plate. Each bar represents mean+SD of triplicate determinations from a representative experiment. The Z'-values are as indicated.

FIG. 2b shows photomicrographs from a 384-well plate adhesion assay showing cells remaining adherent, in the presence of 1 mM Mn2+, before (upper panel) and after (lower panel) automated plate washing.

FIG. 2c shows photomicrographs from a 384-well plate assay showing cells remaining adherent upon completion of the no-wash cell adhesion assay. Cell adhesion to the uncoated well surface is shown (no block).

FIG. 2d shows the number of adherent cells as a function of Fg coating concentration. Each bar represents mean+SD of triplicate determinations from a representative experiment. Automated microscope coupled with image analysis software was used to quantify the adherent cells.

FIG. 2e shows analysis of the assay variability in the no-wash 384-well assay as measured by quantitation of the adherent cells using automated microscope (left panel), or MTS assay (right panel). Each bar represents mean+SD across 192 wells from a representative experiment.

DETAILED DESCRIPTION OF THE INVENTION

Compounds

Figure 3:
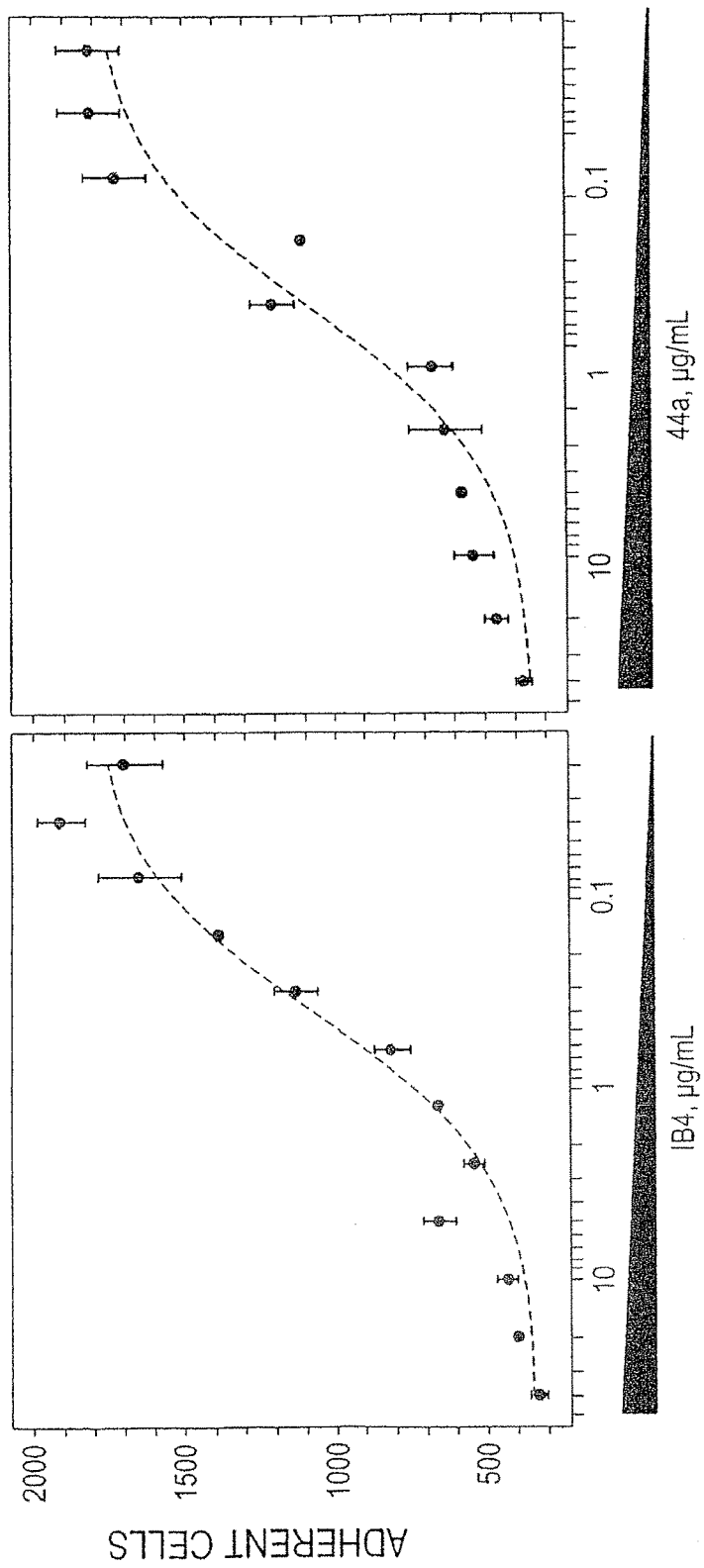
FIG. 3 shows dose-response curves depicting number of adherent cells in the presence of increasing amount of blocking mAbs (IB4, left panel; 44a, right panel). Concentration of mAb used is indicated at the bottom. Curve fitting was done using XLfit4 to show a dose dependent inhibition of cell adhesion in the presence of 1 mM Mn2+. Each dot represents mean+SEM of triplicate determinations from a representative experiment.

One aspect of the invention relates to a compound of Formula (I)

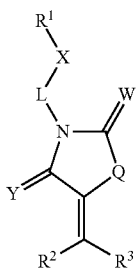

wherein
L is absent or is alkyl;
Q, W, and Y are independently selected from O and S;
X is absent or is selected from O, S, and $NR^4$;
$R^1$ is selected from hydrogen, acyl, alkyl, alkenyl, alkynyl, aryl, heteroaryl, carbocyclyl, heterocyclyl, alkoxycarbonyl, alkylaminocarbonyl, alkylthiocarbonyl, sulfonate, sulfone, sulfoxide, and sulfonamide;
one of $R^2$ and $R^3$ is selected from alkyl, hydroxyalkyl, aminoalkyl, thioalkyl, alkoxyalkyl, aryl, aralkyl, heteroaryl, heteroaralkyl, carbocyclyl, carbocyclylalkyl, heterocyclyl, and heterocyclylalkyl;
the other of $R^2$ and $R^3$ is selected from hydrogen and alkyl, preferably $R^2$ is hydrogen; and
$R^4$ is selected from hydrogen and alkyl, preferably hydrogen.

In certain embodiments, Q and W are S and Y is O. In certain other embodiments, Q and Y are O and W is S.

In certain embodiments, L is alkyl and X is absent or is NR4. In certain such embodiments, R1 is selected from aryl, heteroaryl, carbocyclyl, heterocyclyl and alkoxycarbonyl. In certain such embodiments where L is alkyl and X is absent, R1 is selected from carbocyclyl and heterocyclyl, preferably heterocyclyl. In certain such embodiments where L is alkyl and X is NR4, R1 is selected from aryl and heteroaryl, preferably aryl. In certain embodiments, where L is alkyl and X is absent, R1 is alkoxycarbonyl.

In certain embodiments, R1 is selected from tetrahydrofuran, tetrahydrothiophene, pyrrolidine, tetrahydropyran, tetrahydrothiopyran, piperidine, piperazine, and morpholine. In certain such embodiments R1 is selected from tetrahydrofuran, tetrahydrothiophene, and pyrrolidine, preferably tetrahydrofuran.

In certain embodiments, R1 is phenyl, preferably substituted phenyl. In certain such embodiments, R1 is phenyl substituted one to five, preferably one to three, more preferably one or two times. In certain such embodiments, R1 is phenyl substituted with one or two, preferably two substituents independently selected from halogen, nitro, cyano, hydroxyl, thiol, amino, alkoxy, alkylamino, alkylthio, hydroxyalkyl, alkoxyalkyl, aminoalkyl, thioalkyl, and alkyl, more preferably from alkyl and halogen, e.g., from methyl and chloro.

In certain embodiments, one of R2 and R3 is selected from alkyl, hydroxyalkyl, aminoalkyl, thioalkyl, alkoxyalkyl, aryl, aralkyl, heteroaryl, heteroaralkyl, carbocyclyl, carbocyclylalkyl, heterocyclyl, and heterocyclylalkyl. In certain embodiments, one of R2 and R3 is selected from aryl, aralkyl, heteroaryl, heteroaralkyl, carbocyclyl, carbocyclylalkyl, heterocyclyl, and heterocyclylalkyl, preferably aryl, heteroaryl, carbocyclyl, and heterocyclyl. In certain such embodiments, one of R2 and R3 is selected from aryl and heteroaryl.

In certain embodiments, one of R2 and R3 is heteroaryl selected from pyrrole, furan, and thiophene, preferably furan. In certain embodiments, one of R2 and R3 is furan substituted one to three, preferably one to two times, more preferably once. In certain such embodiments, one of R2 and R3 is furan substituted once with a substituent selected from aryl, aralkyl, heteroaryl, heteroaralkyl, carbocyclyl, carbocyclylalkyl, heterocyclyl, and heterocyclylalkyl, preferably aryl, heteroaryl, carbocyclyl, and heterocyclyl. In certain embodiments, one of R2 and R3 is furan substituted once with an aryl group, which itself is optionally substituted, preferably one to two times with halogen, e.g., chlorophenyl or dichlorophenyl.

In certain embodiments, one of R2 and R3 is aryl, preferably phenyl. In certain such embodiments, one of R2 and R3 is phenyl substituted with one or two, preferably two substituents independently selected from halogen, nitro, cyano, hydroxyl, thiol, amino, alkoxy, alkylamino, alkylthio, hydroxyalkyl, alkoxyalkyl, aminoalkyl, thioalkyl, and alkyl. In certain such embodiments, one of R2 and R3 is phenyl substituted once with a halogen, preferably bromo.

In certain embodiments, a compound of Formula I is selected from

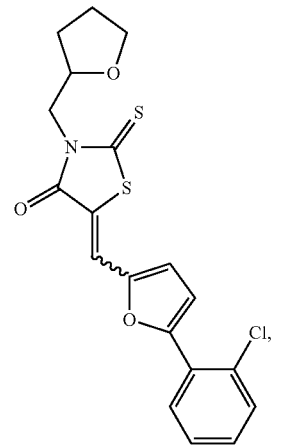

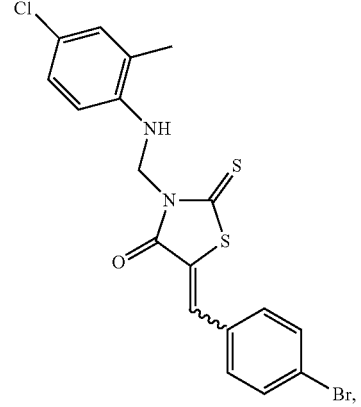

-continued

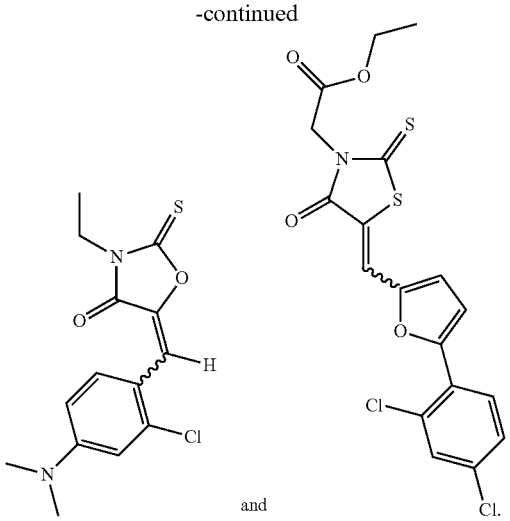

and

One aspect of the invention relates to a compound of Formula (II)

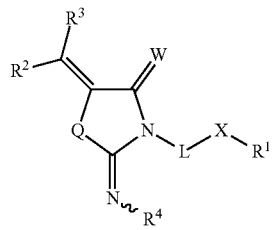
(II)

wherein

L is absent or is alkyl, preferably absent;
Q and W are independently selected from O and S;
X is absent or is selected from O, S, and NR$^5$, preferably absent;
R$^1$ is selected from hydrogen, acyl, alkyl, alkenyl, alkynyl, aryl, heteroaryl, carbocyclyl, heterocyclyl, alkoxycarbonyl, alkylaminocarbonyl, alkylthiocarbonyl, sulfonate, sulfone, sulfoxide, and sulfonamide;
one of R$^2$ and R$^3$ is selected from alkyl, hydroxyalkyl, aminoalkyl, thioalkyl, alkoxyalkyl, aryl, aralkyl, heteroaryl, heteroaralkyl, carbocyclyl, carbocycloalkyl, heterocyclyl, and heterocycloalkyl;
the other of R$^2$ and R$^3$ is selected from hydrogen and alkyl, preferably R$^2$ is hydrogen; and
R$^4$ and R$^5$ are independently selected from hydrogen and alkyl, preferably hydrogen.

In certain embodiments, Q is S and W is O.
In certain embodiments, R1 is selected from hydrogen, aryl, heteroaryl, carbocyclyl, and heterocyclyl, preferably aryl or heteroaryl.
In certain embodiments, R1 is heteroaryl selected from pyrazole, imidazole, oxazole, isoxazole, thiazole, and isothiazole, e.g., thiazole. In certain other embodiments, R1 is hydrogen.
In certain embodiments, R3 is selected from aryl, aralkyl, heteroaryl, heteroaralkyl, carbocyclyl, carbocyclylalkyl, heterocyclyl, and heterocyclylalkyl, preferably aryl, heteroaryl, carbocyclyl, carbocyclylalkyl, and heterocyclyl.
In certain embodiments, R3 is selected from pyrrole, furan, and thiophene, preferably furan. In certain other embodiments, R3 is phenyl substituted with one or two, preferably one substituent selected from halogen, nitro, cyano, hydroxyl, thiol, amino, alkoxy, alkylamino, alkylthio, hydroxyalkyl, alkoxyalkyl, aminoalkyl, thioalkyl, and alkyl.
In certain such embodiments, R3 is phenyl substituted with alkoxy, e.g., wherein the alkoxy group is further substituted with an aryl group, preferably phenyl. In certain such embodiments, R3 is phenyl substituted with alkoxy, wherein the alkoxy group is further substituted with halophenyl, e.g., fluorophenyl.

In certain embodiments, a compound of Formula (II) comprises two aryl or heteroaryl rings, e.g., R3 comprises two aryl or heteroaryl rings, or R3 comprises an aryl or heteroaryl ring and R1 comprises an aryl or heteroaryl ring.

In certain embodiments, a compound of Formula (II) is selected from

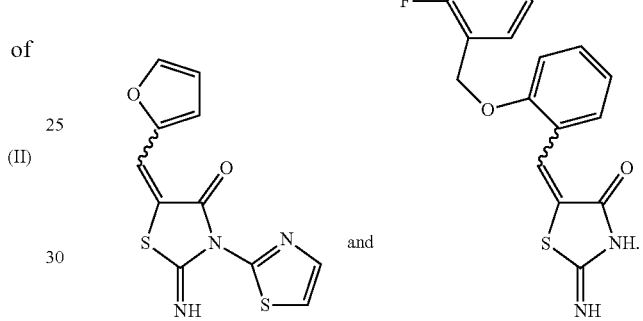

and

One aspect of the invention relates to a compound of Formula (III)

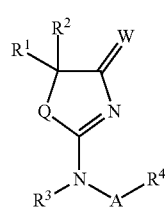
(III)

wherein

A is absent or is selected from C=O, C=S, and SO$_2$, preferably C=O;
Q and W are independently selected from O and S;
R$^1$ and R$^2$ are independently selected from hydrogen, alkyl, alkoxy, alkoxyalkyl, hydroxyalkyl, aminoalkyl, thioalkyl, aralkyl, heteroaralkyl, carbocycloalkyl, and heterocycloalkyl;
R$^3$ is selected from hydrogen and alkyl; and
R$^4$ is selected from alkyl, aralkyl, heteroaralkyl, carbocycloalkyl, heterocycloalkyl, aryl, heteroaryl, carbocyclyl, and heterocyclyl.

In certain embodiments, Q is S and W is O.
In certain embodiments, R1 and R2 are independently selected from hydrogen, alkyl, alkoxy, and alkoxyalkyl, preferably hydrogen and alkyl. In certain such embodiments, R1 and R2 are both hydrogen.
In certain embodiments, R4 is selected from aryl, heteroaryl, carbocyclyl, and heterocyclyl, preferably heteroaryl and heterocyclyl. In certain embodiments, R4 is selected heterocyclyl, preferably comprising at least two, preferably three fused ring structures. In certain embodiments, R4 is selected from phenothiazine and phenoxazine, preferably phenothiazine.

In certain embodiments, a compound of Formula (III) is

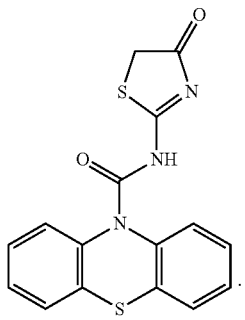 [SMILES: O=C1CSC(NC(=O)N2c3ccccc3Sc3ccccc32)=N1]

One aspect of the invention relates to a compound of Formula (IV)

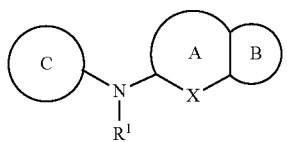

wherein
A and B are independently 5- or 6-membered ring selected from aryl, carbocycle, heterocycle, and heteroaryl, wherein A and B together form a fused bicyclic ring system;
C is a 5- or 6-membered ring selected from aryl, carbocycle, heterocycle, and heteroaryl;
X is selected from $C(R^2)(R^3)$, $N(R^4)$, S, and O, preferably $C(R^2)(R^3)$ and $N(R^4)$;
Z is selected from O, S, and $NR^5$, preferably O;
$R^1$ is selected from hydrogen, alkyl, and aralkyl;
$R^2$ is selected from hydrogen, alkyl, alkoxy, alkoxyalkyl, amino, aminoalkyl, hydroxy, hydroxyalkyl, thiol, and thioalkyl; or
$R^1$ and $R^2$ together are $C_{1-3}$alkyl or —$C_{1-2}$alkyl-Z, thereby forming a 5- to 6-membered ring that is fused to A;
$R^3$ is absent or is selected from hydrogen, alkyl, alkoxy, alkoxyalkyl, amino, aminoalkyl, hydroxy, hydroxyalkyl, thiol, and thioalkyl;
$R^4$ is absent or is selected from hydrogen, alkyl, aryl, aralkyl, heteroaryl, heteroaralkyl, carbocyclyl, carbocycloalkyl, heterocyclyl, and heterocycloalkyl, preferably $R^4$ is absent; and
$R^5$ is selected from hydrogen, alkyl, aryl, aralky, heteroaryl, heteroaralkyl, carbocyclyl, carbocycloalkyl, heterocyclyl, and heterocycloalkyl.

In certain embodiments, A is a 5- or 6-membered ring selected from aryl and heteroaryl. In certain such embodiments, A is a 6-membered ring selected from aryl and heteroaryl. In certain such embodiments, A is heteroaryl and X is N(R4), wherein R4 is absent. In certain such embodiments A is selected from pyridine, pyridazine, pyrazine, and pyrimidine, preferably pyrazine. In certain such embodiments, the pyrazine ring is substituted with a halogen, preferably chloro.

In certain such embodiments, B is a 5- or 6-membered ring selected from aryl and heteroaryl. In certain such embodiments, B is a 5-membered heteroaryl ring. In certain such embodiments, B is selected from pyrrole, furan, thiophene, pyrazole, imidazole, and furazan, preferably furazan. In certain such embodiments R1 is hydrogen.

In certain embodiments, A is 5- or 6-membered ring selected from carbocyclyl and heterocyclyl. In certain embodiments, A is a 6-membered ring selected from carbocyclyl and heterocyclyl. In certain such embodiments, A is a cyclohexa-2,5-dienone.

In certain embodiments, where A is a cyclohexa-2,5-dienone, X is C(R2)(R3). In certain such embodiments, R3 is selected from hydrogen, alkyl, alkoxy, and hydroxy, preferably hydroxy. In certain such embodiments, R1 and R2 together are C1-3alkyl or —C1-2alkyl-Z, thereby forming a 5- to 6-membered ring that is fused to A, preferably R1 and R2 together are —C1-2alkyl-Z, wherein Z is O.

In certain such embodiments, B is a 5- or 6-membered ring selected from aryl and heteroaryl. In certain such embodiments, B is aryl, preferably phenyl.

In certain embodiments, C is a 5- or 6-membered ring selected from aryl and heteroaryl. In certain such embodiments, C is a 6-membered ring, preferably aryl. In certain such embodiments, C is phenyl or phenyl substituted with a substituent selected from alkyl, alkoxy, alkylamino, and alkylthio, preferably alkyl. In certain embodiments, C is phenyl or methylphenyl.

In certain embodiments, a compound of Formula IV is selected from

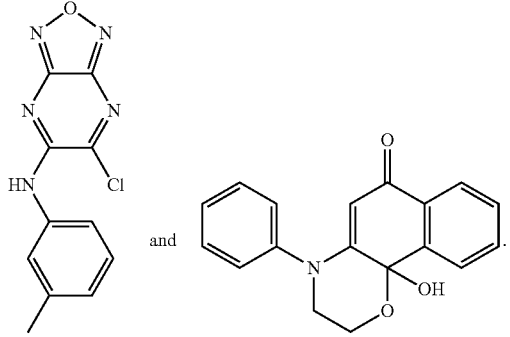 [SMILES: Cc1cccc(Nc2nc3nonc3nc2Cl)c1 ; O=C1C=C2N(c3ccccc3)CCOC2(O)c2ccccc21]

In certain embodiments, the invention relates to a pharmaceutical composition comprising a compound of the invention and a pharmaceutically acceptable diluent or carrier.

In certain embodiments, the invention relates to methods for treating a disease or condition selected from inflammation (including, but not limited to, inflammatory skin diseases and inflammatory bowel disease), immune-related disorders, autoimmune diseases (such as rheumatoid arthritis), cancer, ischemia-reperfusion injury (including, but not limited to, acute renal failure, atherosclerosis, autoimmune disorders, and tissue damage), stroke, shock, myocardial infarction, neointimal thickening associated with vascular injury, bullous pemphigoid, neonatal obstructive nephropathy, cardiovascular disease, immune deficiency, acquired immune deficiency syndrome (AIDS), myeloperoxidase deficiency, Wiskott-Aldrich syndrome, chronic granulomatous disease, hyper-IgM syndromes, leukocyte adhesion deficiency, Chediak-Higashi syndrome, and severe combined immunodeficiency, comprising administering a compound of any one of Formulae I to IV. In certain embodiments, the compound is selected from
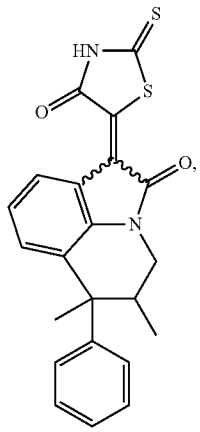
1
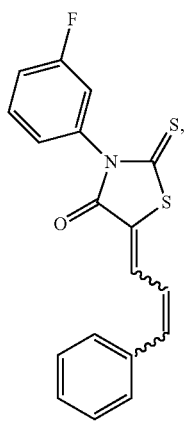
2
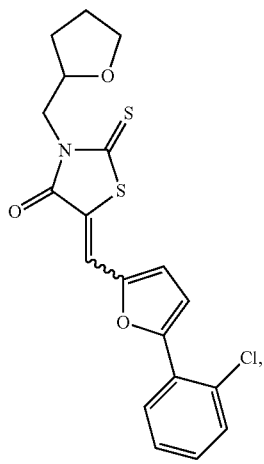
4
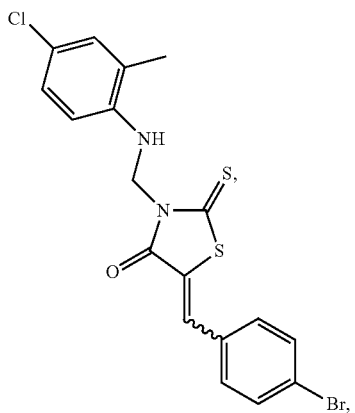
5
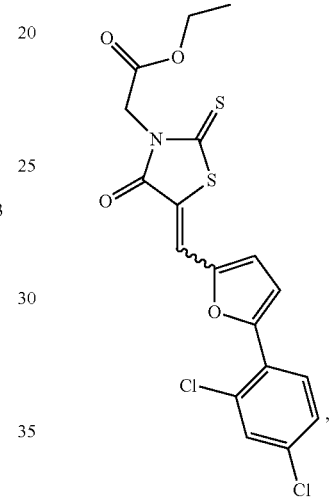
6
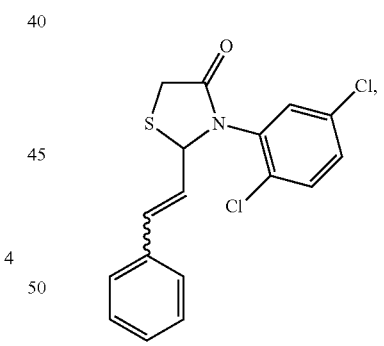
7
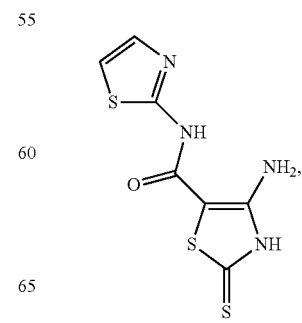
8

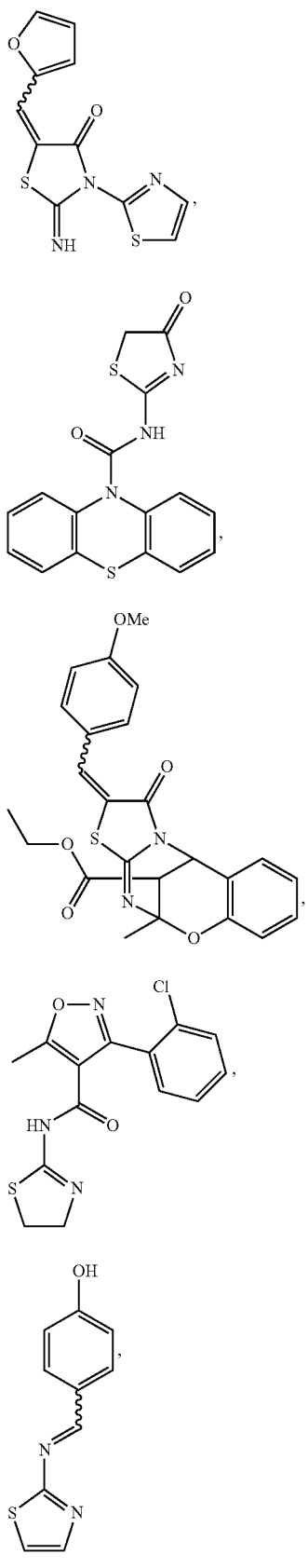
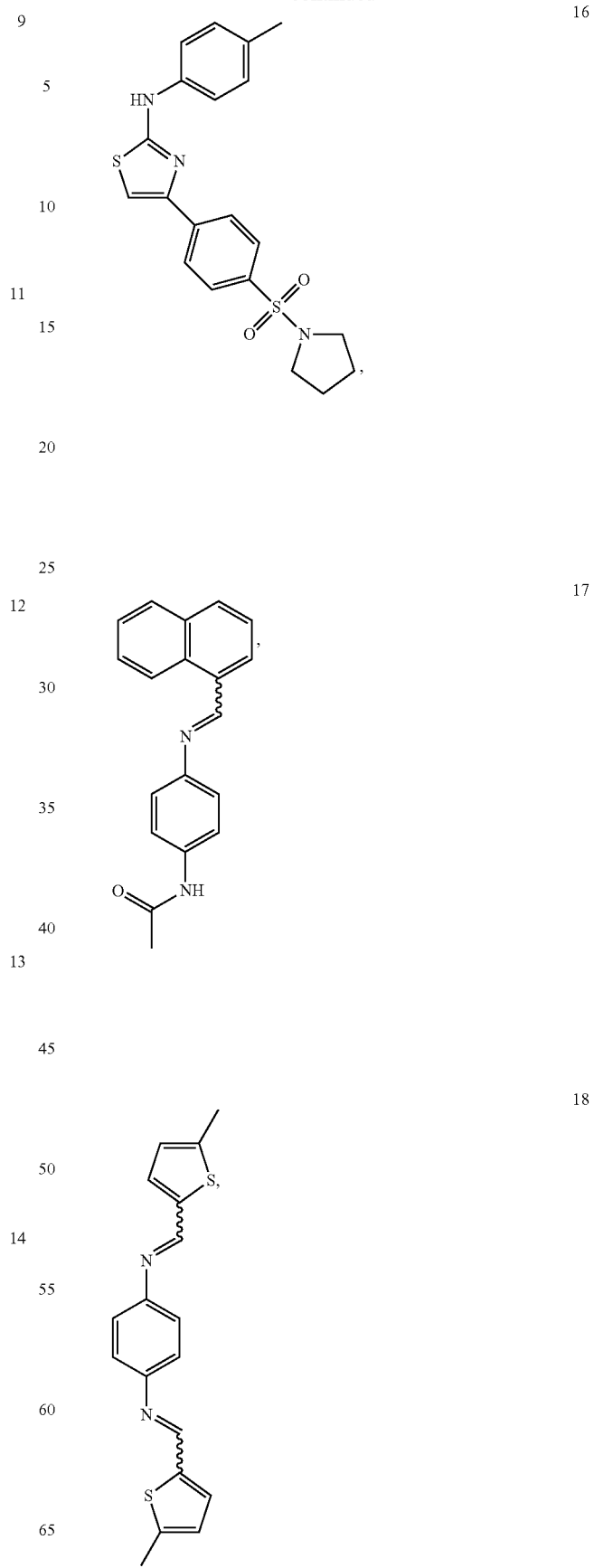

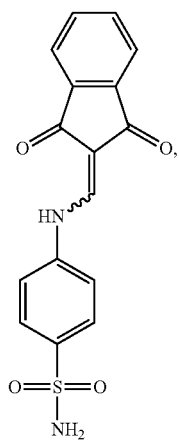
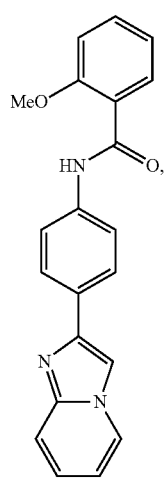
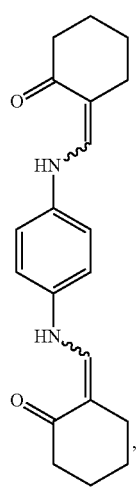
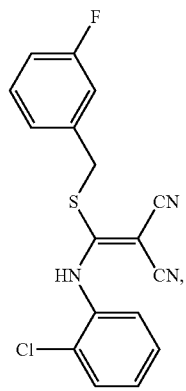
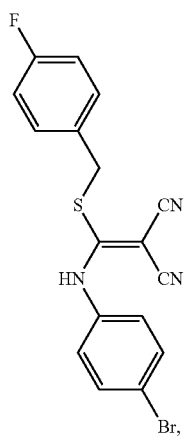
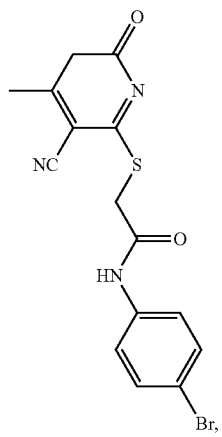
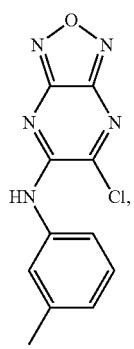

-continued

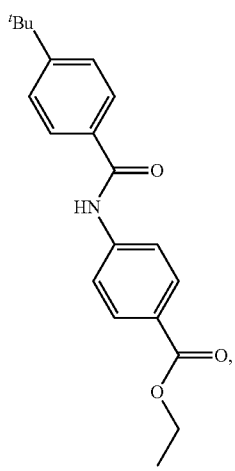
26

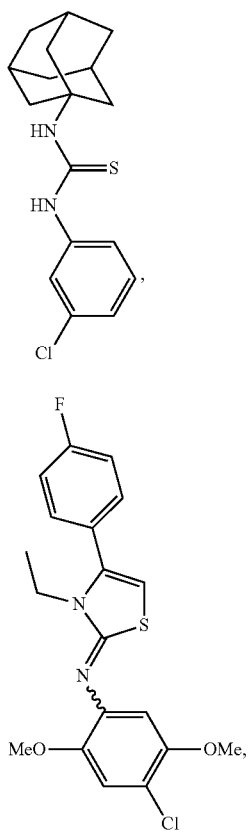
27

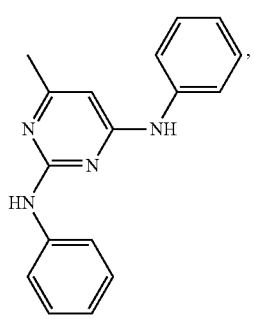
31

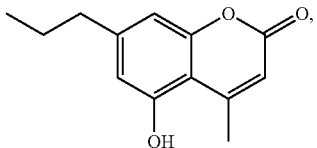
34

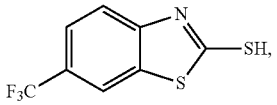
36

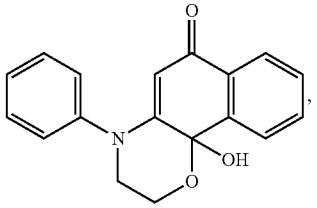
38

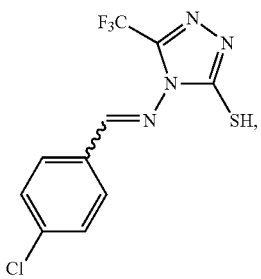
39

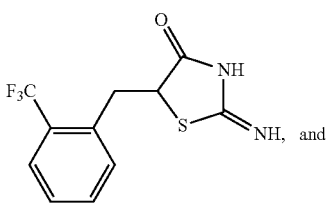
40

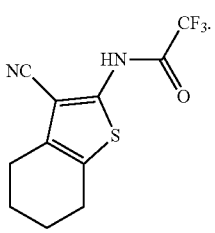
41

In certain embodiments, the invention relates to methods for the treatment of a disease or condition selected from immune deficiency, acquired immune deficiency syndrome (AIDS), myeloperoxidase deficiency, Wiskott-Aldrich syndrome, chronic granulomatous disease, hyper-IgM syndromes, leukocyte adhesion deficiency, Chediak-Higashi syndrome, and severe combined immunodeficiency, comprising administering an agonist of integrin CD11b/CD18. In certain embodiments, the integrin CD11b/CD18 agonist is a compound of any one of Formulae I to III. In certain such embodiments, the integrin CD11b/CD18 agonist is selected from 1
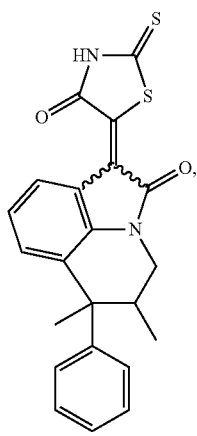
2
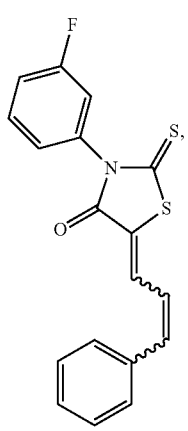
4
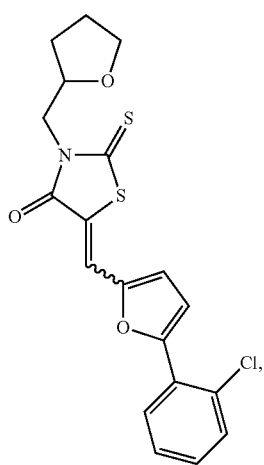
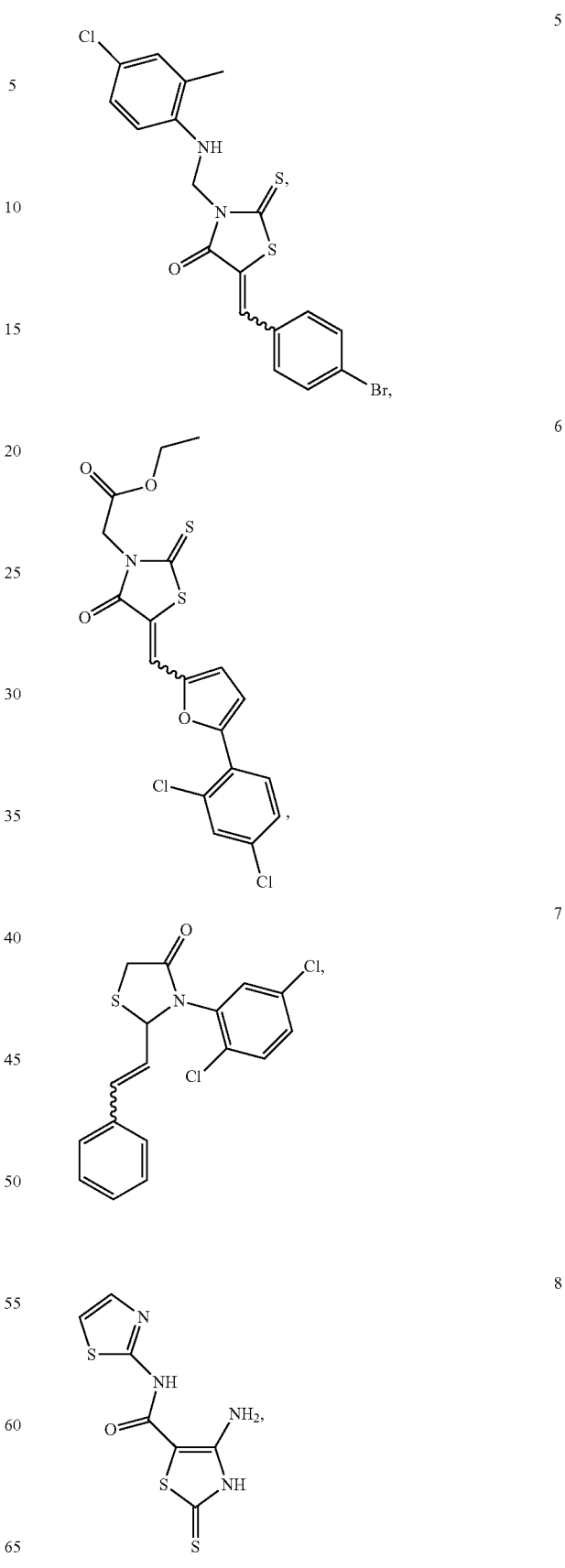

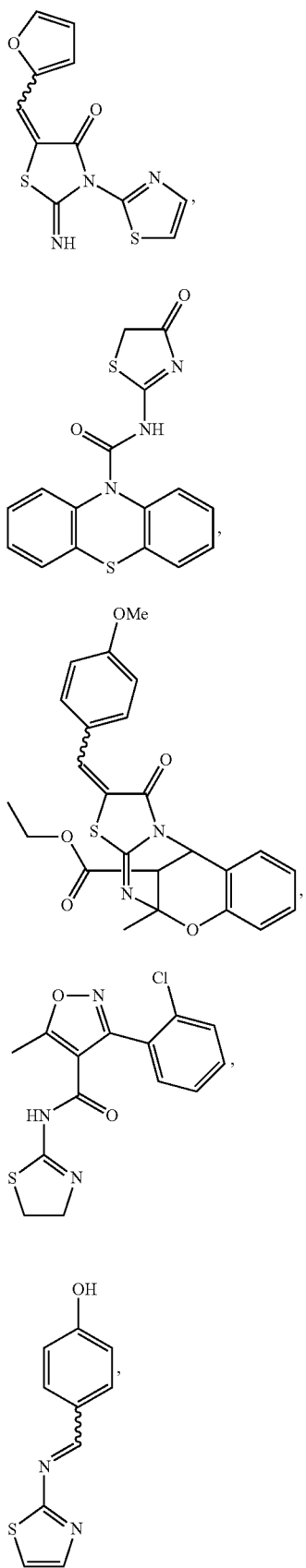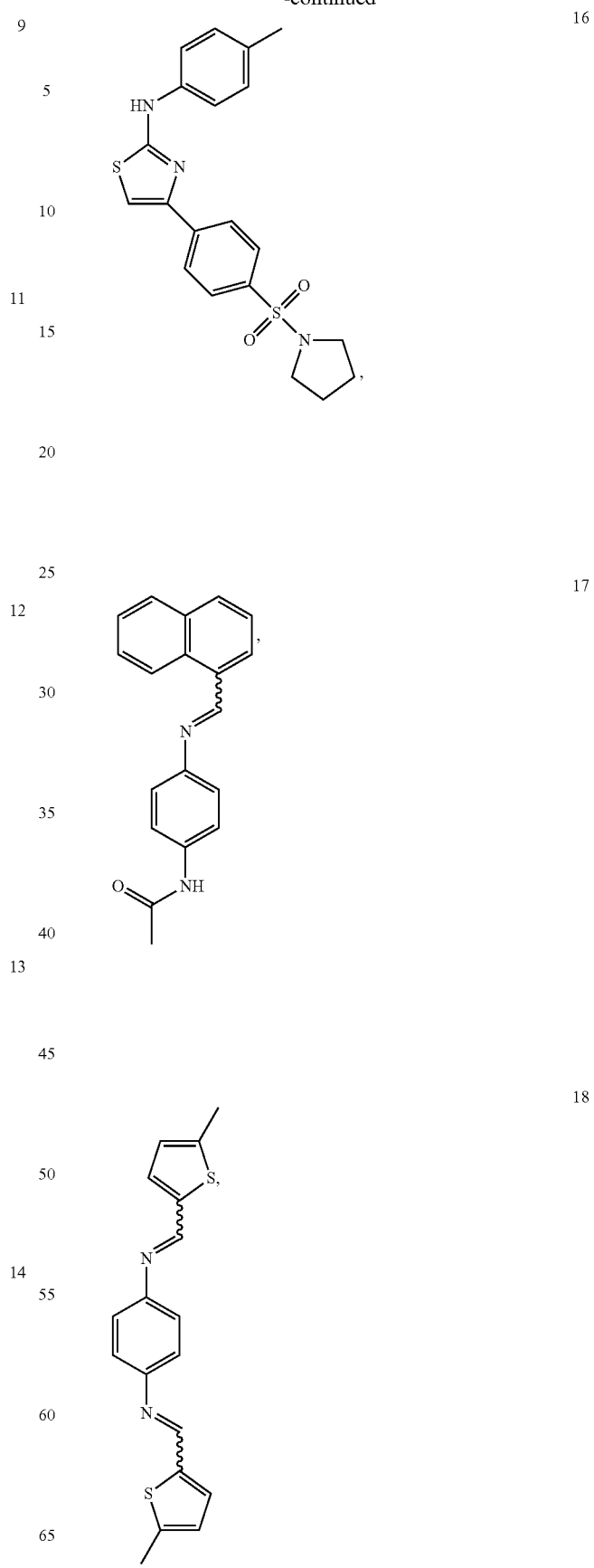

-continued

19

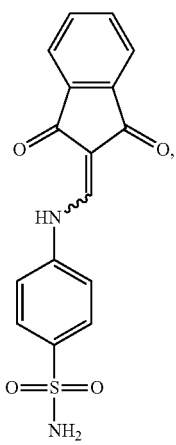

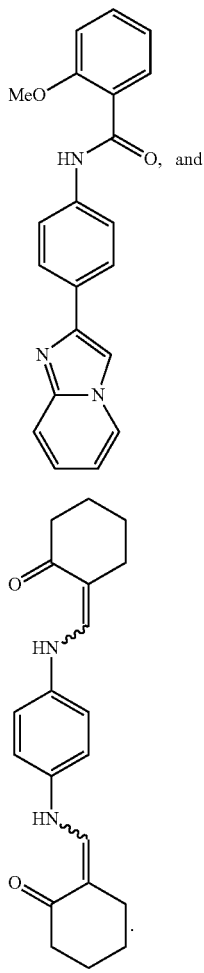

In certain embodiments, the invention relates to methods for the treatment of a disease or condition selected from inflammation (including, but not limited to, inflammatory skin diseases and inflammatory bowel disease), immune-related disorders, autoimmune diseases (such as rheumatoid arthritis), cancer, ischemia-reperfusion injury (including, but not limited to, acute renal failure, atherosclerosis, autoimmune disorders, and tissue damage), stroke, shock, myocardial infarction, neointimal thickening associated with vascular injury, bullous pemphigoid, neonatal obstructive nephropathy, and cardiovascular disease, comprising administering an antagonist of integrin CD11b/CD18. In certain embodiments, the antagonist of integrin CD11b/CD18 is a compound of Formula IV. In certain such embodiments, the antagonist of integrin CD11b/CD18 is selected from

22

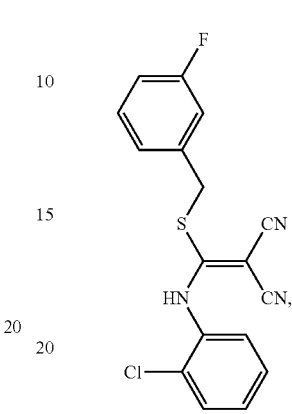

23

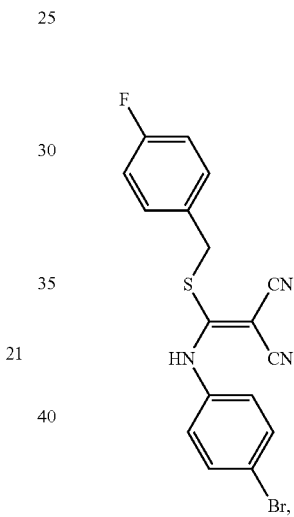

24

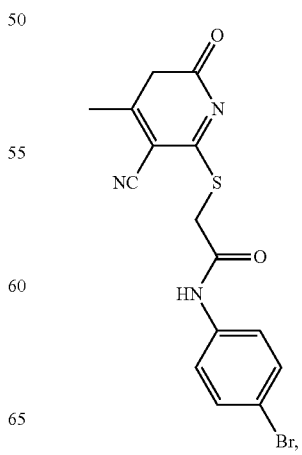

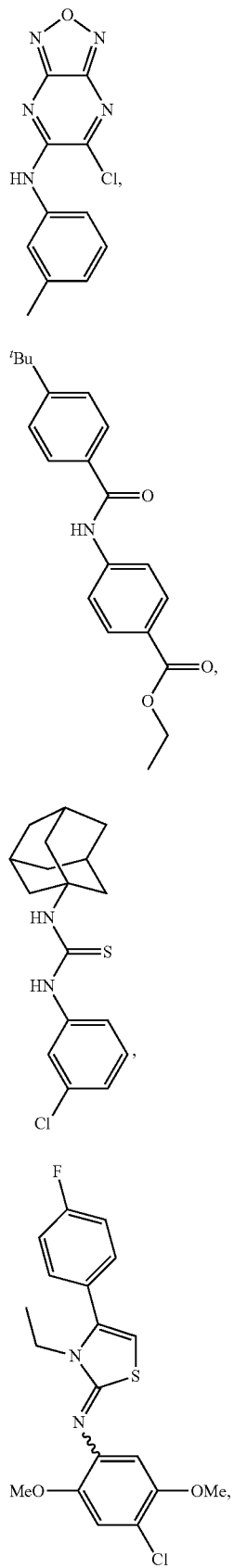
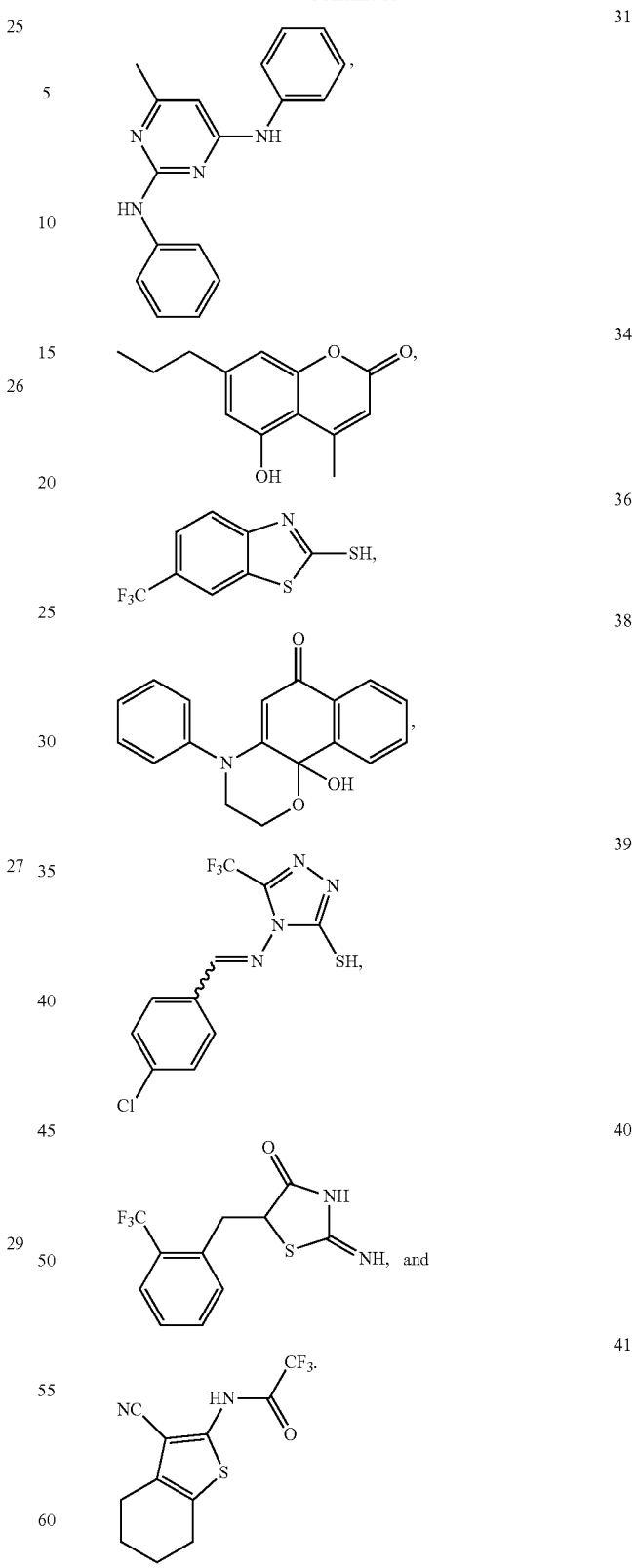
In certain embodiments, the invention relates to methods for the modulation of integrin CD11b/CD18 comprising administering a compound of the invention. In certain such embodiments, the compound of the invention is a compound of any one of Formulae I to IV. In certain embodiments, the invention relates to a method for modulating integrin CD11b/CD18 comprising administering a compound selected from compounds 1-43 as designated above.

In certain embodiments, the invention relates to methods for agonizing integrin CD11b/CD18, comprising administering a compound of the invention. In certain such embodiments, the compound of the invention is a compound of any one of Formulae I to III. In certain such embodiments, the compound of the invention is selected from

2

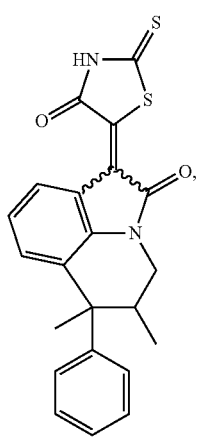

3

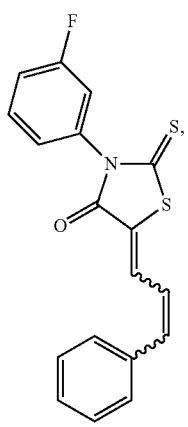

4

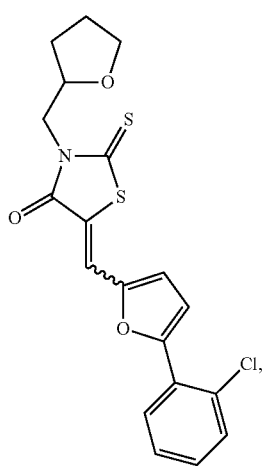

5

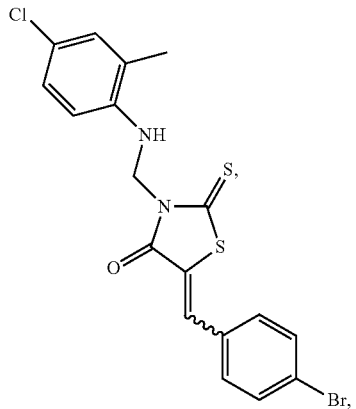

6

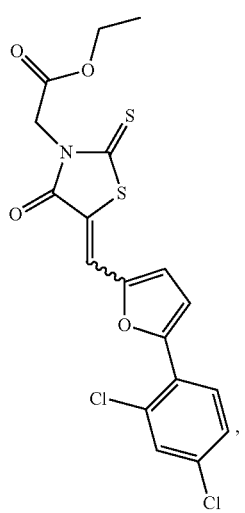

7

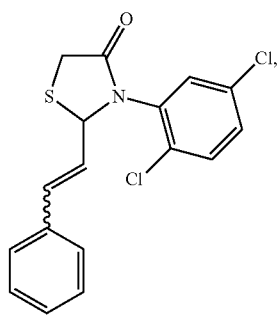

8

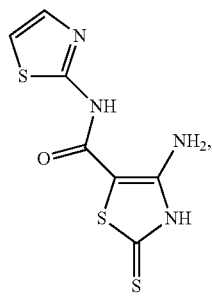

-continued
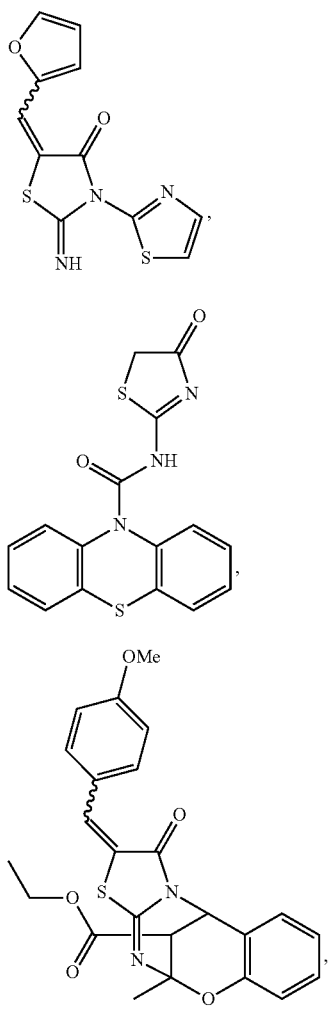
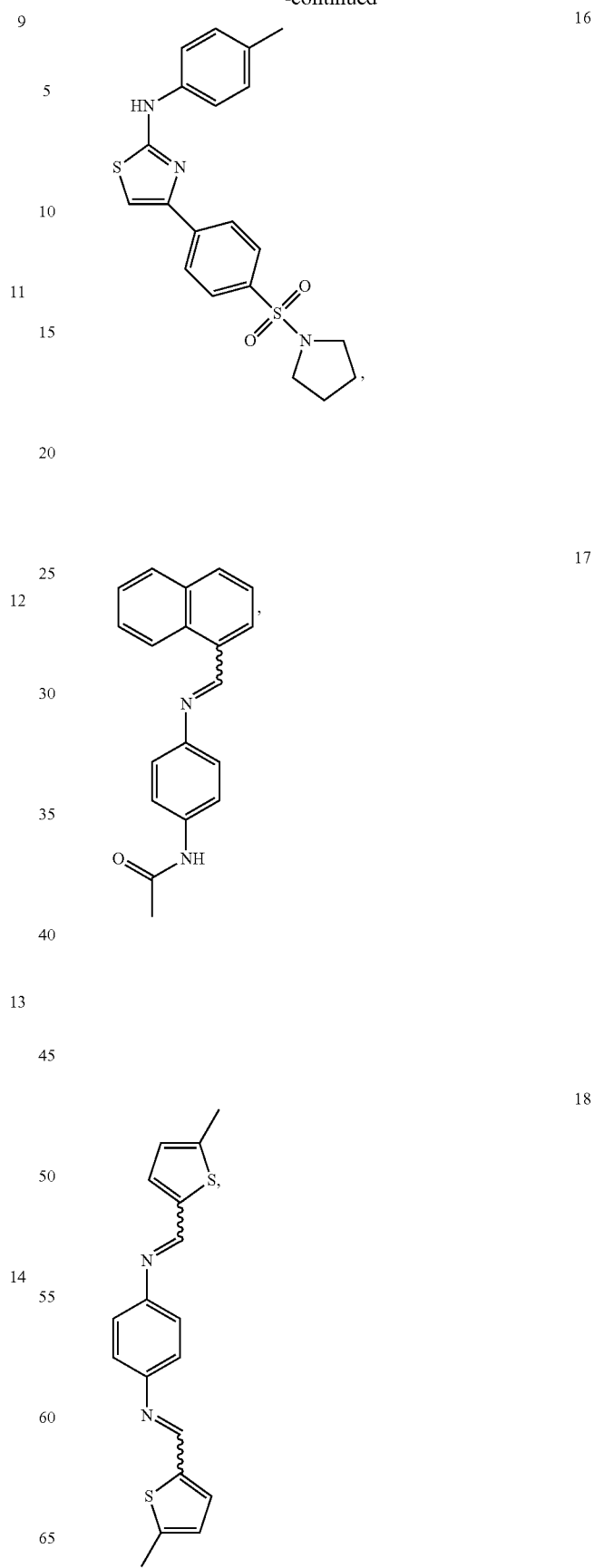

19
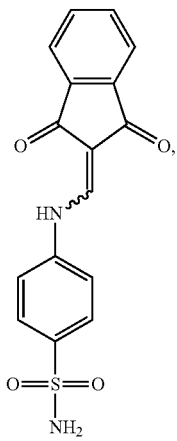
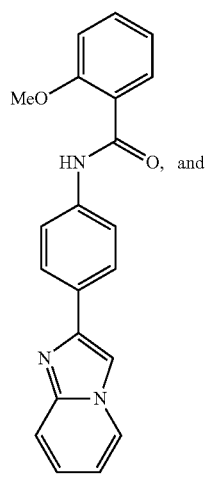, and
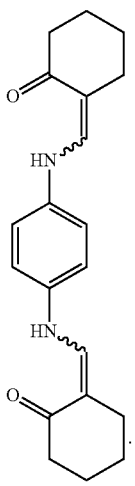
5
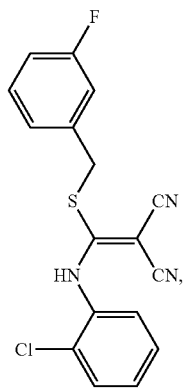
20
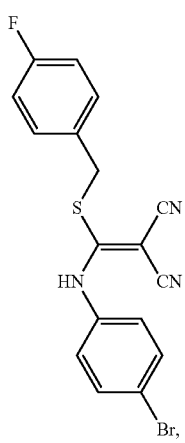
21
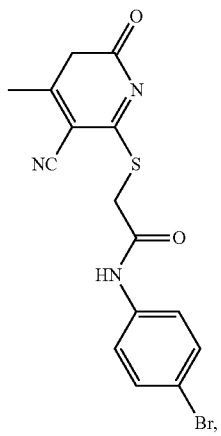
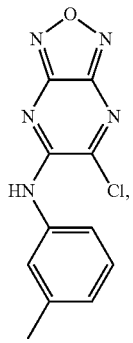
In certain embodiments, the invention relates to methods for inhibiting integrin CD11b/CD18, comprising administering a compound of the invention. In certain such embodiments, the compound of the invention is a compound of Formula IV. In certain such embodiments, the compound of the invention is selected from

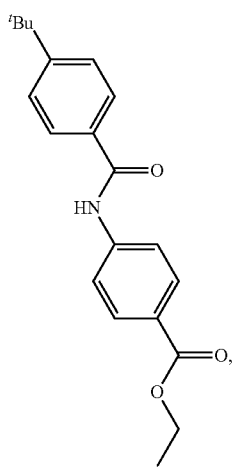

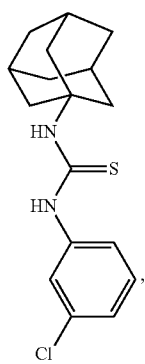

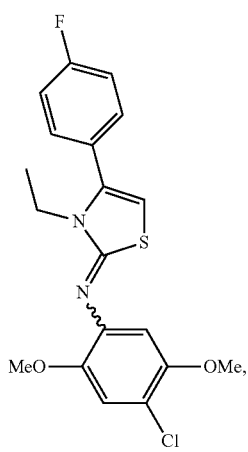

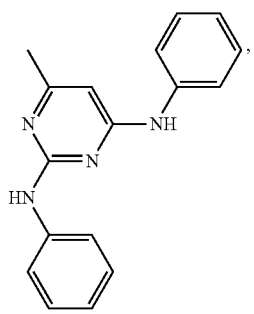

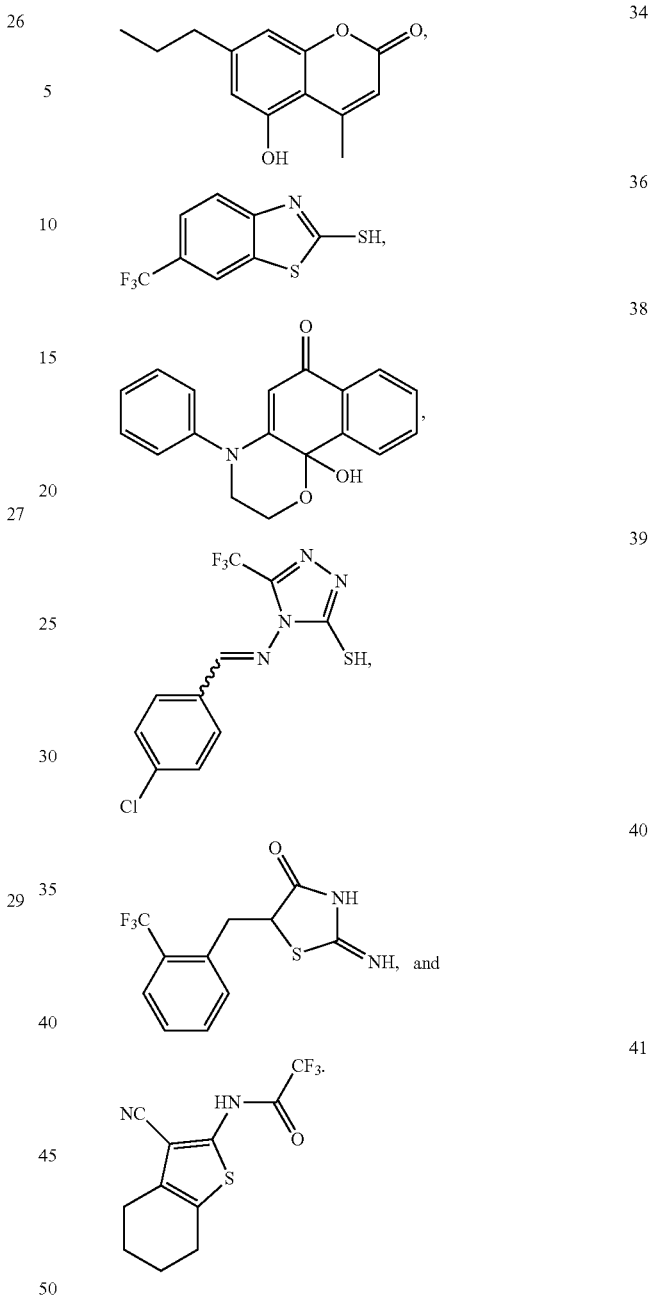

Certain compounds of the present invention may exist in particular geometric or stereoisomeric forms. The present invention contemplates all such compounds, including cis- and trans-isomers, R- and S-enantiomers, diastereomers, (d)-isomers, (l)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts may be formed with an appropriate optically active acid or base, followed by resolution of the diastereomers thus formed by fractional crystallization or chromatographic means well known in the art, and subsequent recovery of the pure enantiomers.

The present invention includes radiolabeled forms of compounds of the invention, for example, compounds of the invention labeled by incorporation within the structure 3H or 14C or a radioactive halogen such as 125I.

In certain embodiments, the invention relates to an assay for the identification of small molecule modulators of integrin CD11b/CD18. In certain embodiments, the assay is a cell-adhesion-based high-throughput screening assay. In certain such embodiments, the assay is a no-wash cell-adhesion-based high-throughput screening assay, which may, for example, be performed in a 96- or 384-well plate format. For example, after contacting cells with a solution comprising a test compound on a substrate treated with a compound that affects (e.g., promotes) cell adhesion (such as a ligand for integrin CD11b/CD18), the substrate may be physically repositioned, e.g., tilted or inverted, such that non-adherent cells move away from the substrate by the action of gravity. In certain embodiments, the samples are treated with a fixative, such as formaldehyde. In certain embodiments, the assay can be performed without contacting the substrate with an additional liquid, e.g., to wash or rinse the substrate. Cells adhering to the substrate can be detected by techniques well known in the art, such as staining or label detection or the use of a cell counting reagent, and the results compared with a control experiment where a test compound was not included.

Alternatively, after contacting cells with a solution comprising a test compound on a substrate, the solution may be removed from the substrate, e.g., by suction, such as by a robotic apparatus, where, after the removal of the liquid phase, cells adhering to the substrate can be detected by techniques well known in the art, such as staining or label detection or the use of a cell-counting reagent, and the results compared with a control experiment where a test compound was not included. In certain embodiments, the samples are treated with a fixative, such as formaldehyde, prior to removal of the liquid phase from the substrate. In certain embodiments, the assay can be performed without contacting the substrate with an additional liquid, e.g., to wash or rinse the substrate. While such assays are demonstrated herein for identifying agonists or antagonists of integrin C11b/CD18, such assays can be employed to identify compounds that inhibit or enhance cell adhesion mediated by other mechanisms as well, as will be recognized by those of skill in the art.

Definitions

The term "alkoxy" refers to an alkyl group having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkyl" refers to saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., C1-30 for straight chains, C3-30 for branched chains), and more preferably 20 or fewer.

Moreover, the term "alkyl" as used throughout the specification, examples, and claims is intended to include both unsubstituted and substituted alkyl groups, the latter of which refers to alkyl moieties having substituents replacing a hydrogen on one or more carbons of the hydrocarbon backbone, including haloalkyl groups such as trifluoromethyl and 2,2,2-trifluoroethyl, etc.

The term "Cx-y" when used in conjunction with a chemical moiety, such as, acyl, acyloxy, alkyl, alkenyl, alkynyl, or alkoxy is meant to include groups that contain from x to y carbons in the chain. C0alkyl indicates a hydrogen where the group is in a terminal position, a bond if internal. A C1-6alkyl group, for example, contains from one to six carbon atoms in the chain.

The terms "amine" and "amino" are art-recognized and refer to both unsubstituted and substituted amines and salts thereof, e.g., a moiety that can be represented by

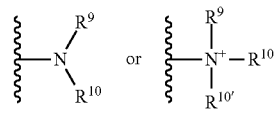

wherein $R^9$, $R^{10}$, and $R^{10'}$ each independently represent a hydrogen or a hydrocarbyl group, or $R^9$ and $R^{10}$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The terms "carbocycle", "carbocyclyl", and "carbocyclic", as used herein, refers to a non-aromatic saturated or unsaturated ring in which each atom of the ring is carbon. Preferably a carbocycle ring contains from 3 to 10 atoms, more preferably from 5 to 7 atoms.

The term "carbocycloalkyl", as used herein, refers to an alkyl group substituted with a carbocycle group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The term "heteroaralkyl", as used herein, refers to an alkyl group substituted with a hetaryl group.

The term "heteroaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The term "heteroaryl" also includes polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The term "heterocycloalkyl", as used herein, refers to an alkyl group substituted with a heterocycle group.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

The term "thioalkyl", as used herein, refers to an alkyl group substituted with a thiol group.

The term "a cell" as used herein includes a plurality of cells. Administering a compound to a cell includes in vivo, ex vivo, and in vitro administration.

To "inhibit" or "suppress" or "reduce" a function or activity, such as cancer cell proliferation, is to reduce the function or activity when compared to otherwise same conditions except for a condition or parameter of interest, or alternatively, as compared to another conditions.

The term "modulate" as used herein includes the inhibition or suppression of a function or activity (such as cell proliferation) as well as the enhancement of a function or activity.

The phrase "pharmaceutically acceptable" is art-recognized. In certain embodiments, the term includes compositions, excipients, adjuvants, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filter, diluent, excipient, solvent or encapsulating material useful for formulating a drug for medicinal or therapeutic use. Each carrier must be "acceptable" in the sense of being compatible with other ingredients of the formulation and not injurious to the patient.

Some examples of materials which can serve as pharmaceutically acceptable carriers include (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically acceptable salt" means an acid addition salt or a basic addition salt which is suitable for or compatible with the treatment of patients.

The term "pharmaceutically acceptable acid addition salt" as used herein means any non-toxic organic or inorganic salt of any base compounds represented by Formula I or II. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of compounds of Formula I or II are more soluble in water and various hydrophilic organic solvents, and generally demonstrate higher melting points in comparison to their free base forms. The selection of the appropriate salt will be known to one skilled in the art. Other non-pharmaceutically acceptable salts, e.g. oxalates, may be used, for example, in the isolation of compounds of Formula I or II for laboratory use, or for subsequent conversion to a pharmaceutically acceptable acid addition salt.

The term "pharmaceutically acceptable basic addition salt" as used herein means any non-toxic organic or inorganic base addition salt of any acid compounds represented by Formula I or II or any of their intermediates. Illustrative inorganic bases which form suitable salts include lithium, sodium, potassium, calcium, magnesium, or barium hydroxide. Illustrative organic bases which form suitable salts include aliphatic, alicyclic, or aromatic organic amines such as methylamine, trimethylamine and picoline or ammonia. The selection of the appropriate salt will be known to a person skilled in the art.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "solvate" as used herein means a compound of Formula I or II, or a pharmaceutically acceptable salt of a compound of Formula I or II, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate".

As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The compositions containing the compounds of the invention can be prepared by known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the substances in association with one or more pharmaceutically acceptable vehicles or diluents, and contained in buffered solutions with a suitable pH and iso-osmotic with the physiological fluids.

The compounds of this invention may be used in the form of the free base, in the form of salts, solvates and as hydrates. All forms are within the scope of the invention. Acid addition salts may be formed and provide a more convenient form for use; in practice, use of the salt form inherently amounts to use of the base form. The acids which can be used to prepare the acid addition salts include preferably those which produce, when combined with the free base, pharmaceutically acceptable salts, that is, salts whose anions are non-toxic to the animal organism in pharmaceutical doses of the salts, so that the beneficial properties inherent in the free base are not vitiated by side effects ascribable to the anions. Although pharmaceutically acceptable salts of the basic compounds are preferred, all acid addition salts are useful as sources of the free base form even if the particular salt per se is desired only as an intermediate product as, for example, when the salt is formed only for the purposes of purification and identification, or when it is used as an intermediate in preparing a pharmaceutically acceptable salt by ion exchange procedures.

Pharmaceutically acceptable salts within the scope of the invention include those derived from the following acids; mineral acids such as hydrochloric acid, sulfuric acid, phosphoric acid and sulfamic acid; and organic acids such as acetic acid, citric acid, lactic acid, tartaric acid, malonic acid, methanesulfonic acid, ethanesulfonic acid, benzenesulfonic acid, p-toluenesulfonic acid, cyclohexylsulfamic acid, quinic acid, and the like.

In accordance with the methods of the invention, the described compounds or salts or solvates thereof may be administered to a patient in a variety of forms depending on the selected route of administration, as will be understood by those skilled in the art. The compositions of the invention may be administered orally or parenterally. Parenteral administration includes intravenous, intraperitoneal, subcutaneous, intramuscular, transepithelial, nasal, intrapulmonary, intrathecal, rectal and topical modes of administration. Parenteral administration may be by continuous infusion over a selected period of time.

A compound of the invention or a salt or solvate thereof may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the compound of the invention may be incorporated with excipient and used in the form of ingestible tablets, buccal tablets, troches, capsules, elixirs, suspensions, syrups, wafers, and the like.

A compound of the invention may also be administered parenterally or intraperitoneally. Solutions of a compound of the invention as a free base or pharmacologically acceptable salt or solvate can be prepared in water suitably mixed with a surfactant such as hydroxypropylcellulose. Dispersions can also be prepared in glycerol, liquid polyethylene glycols, DMSO, and mixtures thereof with or without alcohol, and in oils. Under ordinary conditions of storage and use, these preparations contain a preservative to prevent the growth of microorganisms. A person skilled in the art would know how to prepare suitable formulations. Conventional procedures and ingredients for the selection and preparation of suitable formulations are described, for example, in Remington's Pharmaceutical Sciences (1990-18th edition) and in The United States Pharmacopeia: The National Formulary (USP 24 NF19) published in 1999.

The pharmaceutical forms suitable for injectable use include sterile aqueous solutions or dispersion and sterile powders for the extemporaneous preparation of sterile injectable solutions or dispersions. In all cases the form must be sterile and must be fluid to the extent that easy syringeability exists.

The compounds of the invention may be administered to an animal alone or in combination with pharmaceutically acceptable carriers, as noted above, the proportion of which is determined by the solubility and chemical nature of the compound, chosen route of administration and standard pharmaceutical practice.

The dosage of the compounds and/or compositions of the invention can vary depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the compound in the animal to be treated. One of skill in the art can determine the appropriate dosage based on the above factors. The compounds of the invention may be administered initially in a suitable dosage that may be adjusted as required, depending on the clinical response.

Exemplification

In Vitro Results
Reagents and Antibodies

Restriction and modification enzymes were obtained from New England Biolabs (Beverly, Mass.), GIBCO BRL (Gaithersburg, Md.) or Fisher Scientific. Cell culture reagents were from Invitrogen Corp. (San Diego, Calif.) or Fisher Scientific. The anti-CD11b monoclonal antibody (mAb) 44a (IgG2a) has been described previously (Arnaout, M. A. et al., J Clin Invest. 1983; 72:171-179) and is available from ATCC. The heterodimer-specific anti-CD18 mAb IB4 (IgG2a) has also been described previously (Wright, S. D. et al., Proc Natl Acad Sci USA. 1983; 80:5699-5703) and is available from ATCC. The ligand mimic mAb 107 (IgG1) was generated in-house and has also been previously described (Li, R. et al., J Immunol. 2002; 168:1219-1225) and an activation dependent mAb 24 (IgG1) was previously described (Dransfield, I. and Hogg, N., EMBO J. 1989; 8:3759-3765) and is commercially available from Abcam, MA. Isotype control antibodies MOPC-21 (IgG1) and MOPC-173 (IgG2a) and FITC-conjugated goat anti-mouse Ig were obtained from BDPharmingen (San Diego, Calif.). Human fibrinogen (Plasminogen, von Willebrand Factor and Fibronectin depleted) was purchased from Enzyme Research Laboratories (SouthBend, Ind.). MaxiSorp microtiter plates (96- and 384-well) were from Nunc (Nalgene, N.Y.) and non-fat milk was purchased from BioRad (Hercules, Calif.).

Cell Culture and Stable Transfection

Stable transfection of wild-type integrin CD11b/CD18 in K562 cells (ATCC) was performed using published protocols (See Hogg, N. et al. J Clin Invest. 1999; 103:97-106 and Gupta V. et al. Blood. 2007 109:3513-3520).

Briefly, K562 cells (K562 mock) were grown to log phase in Iscove's Modified Dulbecco's Medium (IMDM, CellGro) supplemented with 10% heat-inactivated fetal bovine serum and 50 IU/mL penicillin and streptomycin, at 37° C. and resuspended in serum-free IMDM at ~1×107/mL. A total of 0.5 mL of cells were transferred into a 0.4-cm cuvette (Fisher), and 10 g each of linearized wild-type CD11b and wild-type CD18 cDNA pcDNA3 expression vectors carrying a G418-resistance marker was added. Electroporation was carried out at 960 F and 320V (Gene-Pulser, Bio-Rad). Transfectants were allowed to recover in serum-containing media for 48 h and were then selected with 0.5 mg/mL G418 (Invitrogen) for up to two weeks. CD11b/CD18 expressing cells (K562 wild-type) were enriched by FACS Sorting using the heterodimer specific mAb IB4. Sorted cells were cloned by limiting dilution and clones with varying levels of integrin expression were identified by flow cytometry and maintained in IMDM supplemented with 10% heat-inactivated fetal bovine serum, 50 IU/mL penicillin and streptomycin and 1 mg/mL G418.

Flow Cytometry

Flow cytometric analysis of K562 cells (mock and wild-type) was performed using published protocols. Briefly, cells were counted and washed twice with PBS containing 1 mM each of Ca2+ and Mg2+ ions (PBS++). Cells (5×105) were incubated with primary mAb (3 g/mL) in 100 L PBS++ at room temperature for 15 min, except for mAbs 24 and the isotype-matched control mAb MOPC-21, where incubations were performed in Tris Buffered Saline (TBS, Boston Bioproducts) at 37° C. for 30 min and in the presence of either Ca2+ and Mg2+ (1 mM each) or 1 mM Mn2+. Cells were subsequently washed with PBS++ and incubated with FITC-conjugated secondary mAb (5 g/mL) for 20 min at room temperature. Stained cells were washed and analyzed using FACS Scan flow cytometer (BDBiosciences, CA), counting 10,000 events. Data was analyzed using the CellQuest software (BDBiosciences).

Coating Microtiter Plates with Ligand

Maxisorp microtiter plates (96- and 384-well) were coated with 1-20 g/mL fibrinogen (Fg) ligand in PBS++ overnight at 4° C. Subsequently, the Fg-coated wells were washed with TBS and non-specific sites were blocked by incubation with 2% non-fat milk in TBS at room temperature for 30 min. Next, the wells were washed three times with TBS and the coated microtiter plates were used in the HTS assays.

HTS Adhesion Assay

All the adhesion assays were carried out in the screening facility at the Institute of Chemistry and Cell Biology (ICCB), Harvard Medical School using the available small molecule libraries and equipment. Actimol Timtec 1 small molecule library (6,612 compounds) has been previously described (http://iccb.med.harvard.edu/screening/compound_libraries). The small molecule library is stocked in 384-well plates at −80° C. and as sealed plates, with each well's containing a unique compound dissolved in DMSO at approximately 5 mg/mL. For the adhesion assay, the K562 cells were washed with TBS and cells (50,000/well for 96-well plates and 20,000/well for 384-well plates) were transferred to the Fg-coated wells of microtiter plates in the assay buffer (TBS containing 1 mM each of Ca2+ and Mg2+ (TBS++) for agonist identification assays or TBS for antagonist identification assays). Compounds were transferred to each well using pin-transfer robot (Seiko D-TRAN XM3106-31 PN 4-axis cartesian robot) with a 384 transfer pin (VP Scientific) calibrated at 100 mL and the assay plates were incubated at 37° C. in the presence of small molecule compounds. In the screen for agonists, the cells were in TBS++ and were incubated with small molecules for 30 min. In the screen for antagonists, following incubation of the cells in TBS with small molecules for 20 min at 37° C., 1 mM Mn2+ was added to each well and the cells were further incubated for an additional 15 min at 37° C. In order to dislodge the non-adherent cell, the assay plates were gently inverted and kept in the inverted position for 20 min at room temperature. Adherent cells were quantitated using either cell viability measuring reagents or automated imaging (see below).

Quantitation of Adherent Cells

For quantitation of adherent cells using a cell viability measuring kit (such as MTS-based CellTiter-One (Promega), CyQuant (Molecular Probes) or Luciferase-based CellTiter-Glo (Promega)), the non-adherent cells were removed by complete aspiration using an automated liquid handling machine (ELx405, Bio-Tek Instruments, VT) and the assay reagent added according to manufacturer's instructions. For automated imaging based quantitation of adherent cells, the non-adherent cells were fixed by adding a small volume of formaldehyde (1.1% v/v final concentration) and the plates were kept inverted for an additional 1 h. Upon cell fixation, the wells were washed with TBS using automated liquid handling machine (ELx405) and the adherent cells were fluorescently labeled with DAPI (0.5 M final in TBS with 0.1% TritonX-100) and quantitated using automated microscope (see below).

Automated Imaging and Analysis

CellWorx automated microscope (Cellomics, PA) was set at 0.3 s exposure using DAPI filter set to capture 1-3 images per well. Digitized photomicrographs were then analyzed using MetaXpress image analysis software (MolecularDevices, CA) using the built-in cell count module to quantify nuclear staining. Data output files were analyzed using MS Excel.

Calculation of Assay Values and Hit Identification

Using the number of non-small molecule treated cells adherent in basal physiologic buffer condition (1 mM each of Ca2+ and Mg2+) as a minimum threshold, any small molecule resulting in >10-fold increase in cell adhesion was scored as a positive agonist hit. Additionally, using the number of non-small molecule treated cells adherent in activating buffer condition (1 mM Mn2+) as a maximum, any small molecule resulting in 50%-70% decrease in cell adhesion was scored as a positive antagonist hit.

Statistical Analysis and Curve Fitting

Regression lines were plotted using XLfit4 (ID Business-Solutions, MA) and EC50 and IC50 values were calculated using GraphPad Prism (SanDiego, Calif.) with four parameter logistic curve fitting using the formula:

$$y=\min+(\max-\min)/(1+10(\log EC50-x)\text{hillslope}).$$

All data are reported as mean±SEM. Z'-factor was calculated as previous described.

Expression of Heterodimeric CD11b/CD18 on K562 Cell Surface

Erythroleukemic K562 cells were chosen for the adhesion assay, as these cells express integrins, native or recombinant, in a default low affinity state similar to normal leukocytes and, as with leukocytes, the expressed integrins can be activated and made ligand-competent by various external stimuli. Thus, these cells provide an excellent context for the discovery of small molecule regulators of integrin function. The K562 cells, which do not endogenously express the integrin CD11b/CD18, were transfected with wild type CD11b/CD18 using electroporation and several single cell clones stably expressing the integrin CD11b/CD18 on the cell surface were obtained by FACS sorting using heterodimer-specific mAb 1B4 (See McDowall, A. et al., J Clin Invest. 2003; 111:51-60), as has been previously described (See Gupta V. et al. Blood. 2007 109:3513-3520 and Annenkov, A. et al., Eur J Immunol. 1996; 26:207-212). Several different clones displaying varying levels of CD11b/CD18 surface expression were also obtained and characterized (FIG. 1A), as these clones would be useful in the future for performing dose response curves to study the dependence of integrin density on the effect of various small molecule compounds identified from this screen. One clone, designated 3F9, was selected and the CD11b/CD18 surface expression level on 3F9 was further characterized with anti-CD11b mAb 44a and with a ligand mimetic mAb 107, both of which showed binding comparable to that observed with the mAb IB4 (FIG. 1B).

The K562 Cell-surface Expressed Integrin CD11b/CD18 was Functionally Active.

K562 cells express wild-type integrin in a largely inactive state, which can be activated by inside-out signals primarily through a change in integrin affinity rather than avidity. The integrin CD11b/CD18 expression in the correct conformational state on the surface of K562 cells was verified using an activation-sensitive mAb, mAb 24, and using CD11b/CD18 physiologic ligand fibrinogen. The mAb 24 binds to an activation- and cation-dependent epitope in the A and has been widely used as a reporter of the high affinity state in 2 integrins (See Dransfield, I. and Hogg, N., EMBO J. 1989; 8:3759-3765). The binding of mAb 24 to CD11b/CD18 expressed on K562 cells was assessed using flow cytometry (FIG. 1C). Very little binding was seen in the low-affinity integrin conformation in physiologic Ca2+ and Mg2+ (1 mM each) buffer, which reproducibly increased upon activation with 1 mM Mn2+ (FIG. 1C), comparable in magnitude to that observed previously in maximally activated 2 integrins expressed in K562 cells, indicating that the integrins become functionally active in the presence of 1 mM Mn2+.

Adhesion of integrin-expressing cells to ligand-coated plates is a well known assay for the study of integrin function and has been used for the study of numerous integrins, ligands and cell types. Binding of K562 cells to the physiologic CD11b/CD18 ligand fibrinogen (Fg) was analyzed using 96-well plates. Fg is a symmetric dimer that is recognized by a number of different integrins and has been shown to be a critical CD11b/CD18 ligand for inflammatory response and host clearance of microbes. Thus, Fg-CD11b/CD18 interaction is an important target for anti- and pro-inflammatory therapeutic strategies. ELISA-based analysis of Fg-coated wells with anti-Fg mAb showed that the ligand coating of the assay plates was highly even and reproducible and displayed very low variability. K562 cells (50,000/well) in Tris buffered saline (TBS) were added to Fg-coated wells of a 96-well plate, in the presence of EDTA (10 mM), $Ca^{2+}$ and $Mg^{2+}$ (1 mM each), or $Mn^{2+}$ (1 mM), and briefly centrifuged at 500 rpm for 10s. After incubation at 37° C. for 30 min, unbound cells were removed by gentle hand washing and the adherent cells were quantitated using CellTiter-Glo (Promega, Madison, Wis.). In this system, no Fg binding by CD11b/CD18-expressing cells was observed in the presence of EDTA or the physiologic divalent cations $Ca^{2+}$ and $Mg^{2+}$ (FIG. 1D). Activation with 1 mM $Mn^{2+}$ induced a large increase in Fg binding by the CD11b/CD18-expressing cells (FIG. 1D), indicating that the adhesion to Fg was CD11b/CD18 dependent.

Adaptation of Cell Adhesion Assay to a 384-well Format

Next, the 96-well adhesion assay was directly adapted to the 384-well plate format. The assay was performed as described for the 96-well plate assay (above), except that fewer K562 cells (20,000/well) were used and that the final washing step was carried out using an automated plate washer. Although no Fg binding was found by CD11b/CD18-expressing cells in the absence of activating $Mn^{2+}$ ions and activation with 1 mM $Mn^{2+}$ induced a large increase in Fg binding by the CD11b/CD18-expressing cells (FIG. 2A), Z'-values ≥0.5 could not be obtained in spite of every effort to perform the plate washing as gently as possible. In fact, negative Z'-values were obtained from most of the assays, suggesting that this protocol presented high variability and was not compatible with the HTS environment. Examination of the bottom of 384-well plates for visualization of 1 mM $Mn^{2+}$ treated adherent cells using DAPI-staining and photomicrography with an automated microscope revealed that uneven number of cells remained adherent upon completion of the assay and sometimes cells were completely absent from the middle of the wells (FIG. 2B). Upon carefully monitoring the adherent cells in the wells after each step in the assay, it was discovered that the automated washing step caused substantial and uneven detachment of adherent cells from wells. A gentle inversion of the plates provided a method for effectively removing non-adherent cells. For the complete removal of non-adherent cells prior to quantitation of adherent cells, there were two methods developed, both of which gave very similar results.

In the first method, 1.1% formaldehyde was added and the adherent cells were fixed to the bottom of 384-well plates, in the inverted position, for 1 h at room temperature. The wells were subsequently washed using an automated plate washer and the fixed cells were stained with DAPI. DAPI-stained cells were photomicrographed using an automated microscope and the images of stained nuclei were quantitated using MetaXpress following the manufacturer's recommendations. In the second method, using gentle inversion, the supernatant containing non-adherent cells were completely aspirated using an automated plate washer and a developer reagent, such as MTS (which showed the linear dynamic range >2-logs), was added to quantitate cell number. The plates were developed according to the manufacturer's recommendations.

FIG. 2C shows sample photomicrographs from a 384-well plate showing cells adherent to increasing amount of Fg. These photomicrographs show very little Fg binding by CD11b/CD18-expressing cells in the absence of $Mn^{2+}$ and a large increase in binding upon incubation with $Mn^{2+}$ at every Fg coating concentrations tested. Input cell number was estimated by determining cell adhesion to the non-Fg-coated microtiter well surface, which showed high non-specific binding (FIG. 2C, no block). The photomicrographs from triplicate measurements were quantitated using MetaXpress and the results show that the Fg binding by CD11b/CD18-expressing cells was completely dependent upon activating $Mn^{2+}$ ions and that the variability associated with this assay was very low (FIG. 2D). Similarly, binding by CD11b/CD18-expressing cells to a second physiologic ligand iC3b3 showed high selectivity and low variability.

Next, the Z'-values across an entire 384-well plate was measured to determine if the optimized assay was ready for an HTS campaign. FIG. 2E shows that the Z'-values after completion of the adhesion assay were ≥0.5 independent of the method used to quantitate adherent cell number. Although only ~⅙th of each 384-well was photomicrographed using an automated microscope (to keep the imaging and image analysis time to a minimum), whereas the entire well was quantitated using MTS, the Z'-values obtained were very similar with the two readouts, suggesting that this simple protocol presented low variability and high compatibility with the HTS environment.

The specificity of CD11b/CD18-expressing cells towards Fg in this assay format was further confirmed by incubation with anti-CD11b (44a) or anti-CD18 (IB4) blocking mAbs. CD11b/CD18-expressing cells were pretreated with an increasing amount of the blocking mAbs for 15 min at room temperature and then allowed to adhere to Fg-coated wells in the presence of $Mn^{2+}$ (1 mM). After incubation at 37° C. for 30 min, unbound cells were removed and the remaining cells were quantitated using automated microscopy, which showed a dose-dependent inhibition of cell adhesion to Fg (FIG. 3). Both mAbs produced an IC50 value of ~0.5 g/mL (~3.3 nM), which is similar to the published value (2 nM) for mAb 44a. Additionally, very little binding was seen with non-transfected K562 cells under any condition.

Figure 4:
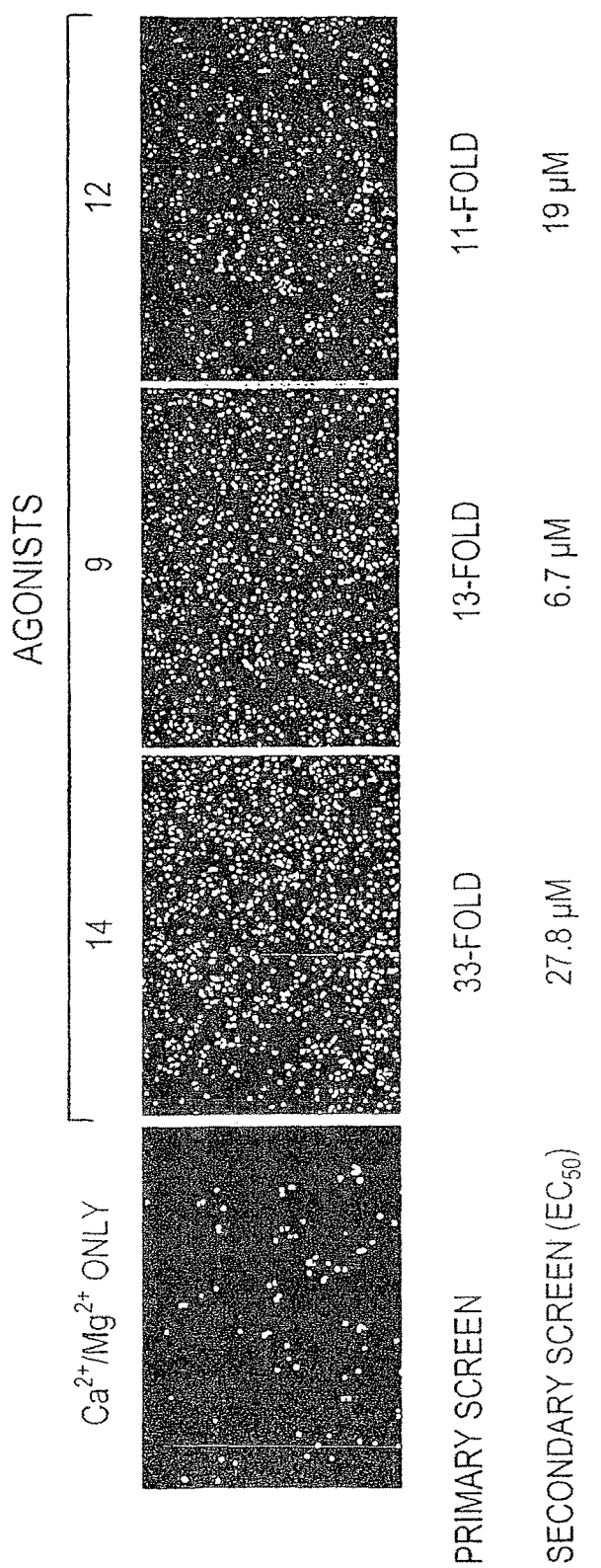
FIG. 4 shows primary and secondary screening data for selected agonists. Photomicrographs from the primary screen show increased cell adhesion caused by treatment with three of the identified agonists in physiological buffer condition. The fold-increase in the number of adherent cells (over Ca2+ and Mg2+ levels) in the presence of the indicated compounds is shown under each panel. The EC50 value for each of the compounds obtained from the secondary screen is also indicated.

Application of the HTS Adhesion Assay for Identification of Small Molecule Agonists and Antagonists The simple, no-wash cell adhesion assay was used to perform a pilot primary screen to identify small molecule agonists and antagonists using a library of ~6,600 compounds (Actimol Timtec1). In the assay for identification of agonists that produce increased cell-adhesion, the cells were transferred to ligand-coated wells of a 384-well plate in TBS buffer containing 1 mM each of $Ca^{2+}$ and $Mg^{2+}$ (TBS++), and compounds were added to each well using a 384 pin-transfer robot. After incubation of the assay plate for 30 min at 37° C., the non-adherent cells were removed by plate inversion and the cell number in each well was quantitated using automated microscopy and image analysis. Large activation and increase in cell-adhesion (>10 fold increase over adhesion by non-treated cells) was shown for 144 compounds (2.2%). While not wishing to be limited by mechanism, it is believed that compounds described herein may act directly on the target protein, rather than through other proteins in the cell. FIG. 4 shows data for three of the compounds that showed high potency in the primary screen (>10-fold increase in cell-adhesion).

Next, 31 compounds were selected from the initial group of 144 for verification in secondary assays. It was found that 28 of these compounds were confirmed agonists (although 4 compounds showed a modest 2-fold increase over the background and are thus weak agonists), producing a hit confirmation rate of approximately 90%. The hit confirmation rate was unusually high for a primary screen and suggests that in spite of using a simple, no-wash protocol, the assay had high sensitivity. Additionally, determination of the concentration required for half-maximal increase in cell-adhesion (EC50) for the three selected agonists showed that even though they displayed similar potency in the primary screen, Compound 9 was the most potent of all with the calculated EC50 value of about 6.7 M (FIG. 4), which is in similar range as other recently identified agonists.

Figure 5:
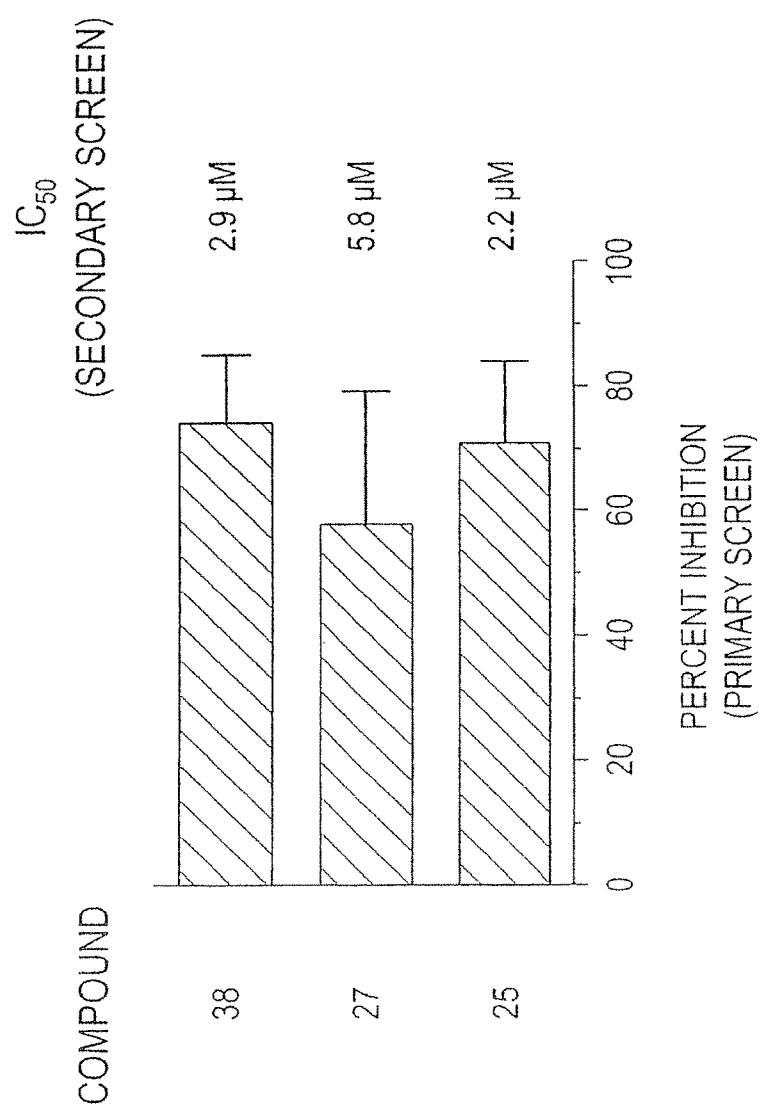
FIG. 5 shows primary and secondary screening data for selected antagonists. Bar graphs show percent inhibition of cell adhesion in the presence of activating Mn2+. Each bar represents mean of duplicate wells. Cell adhesion under physiological condition (TBS++) was considered as maximum inhibition (100%). Cell adhesion observed in the presence of buffer alone (1 mM Mn2+) was assigned a value of 0% (no inhibition). The IC50 value for each of the compounds obtained from the secondary screen is also indicated.

This assay was also used to identify inhibitors of cell-adhesion (antagonists). Non-adherent cells were removed and the cell number in each well was quantitated using MTS. Twenty-two compounds (0.3%) showed significant (50%-70% decrease) and reproducible (duplicate wells) inhibition. FIG. 5 shows data for three of the compounds that showed high potency in the primary screen. The identified compounds contain a planar aromatic substructure, reminiscent of the small molecule inhibitors of CD11a A-domain that occupy the allosteric SILEN-pocket (named IDAS in CD11a).

The 22 compounds were then evaluated in secondary assays, wherein nine of the selected compounds (Compounds 22, 23, 24, 25, 27, 31, 36, 38 and 41) showed more than 50% inhibition of cell-adhesion and were confirmed antagonists, whereas eight compounds showed no effect. Additionally, the secondary assays were inconclusive for five compounds, producing a hit confirmation rate of approximately 53% for antagonists. The three selected antagonists were further characterized in secondary assays, and all three were highly potent and had very similar IC50 values (FIG. 5).

Selectivity for Integrin CD11b/CD18 Over Integrin CD11a/CD18

Figure 6:
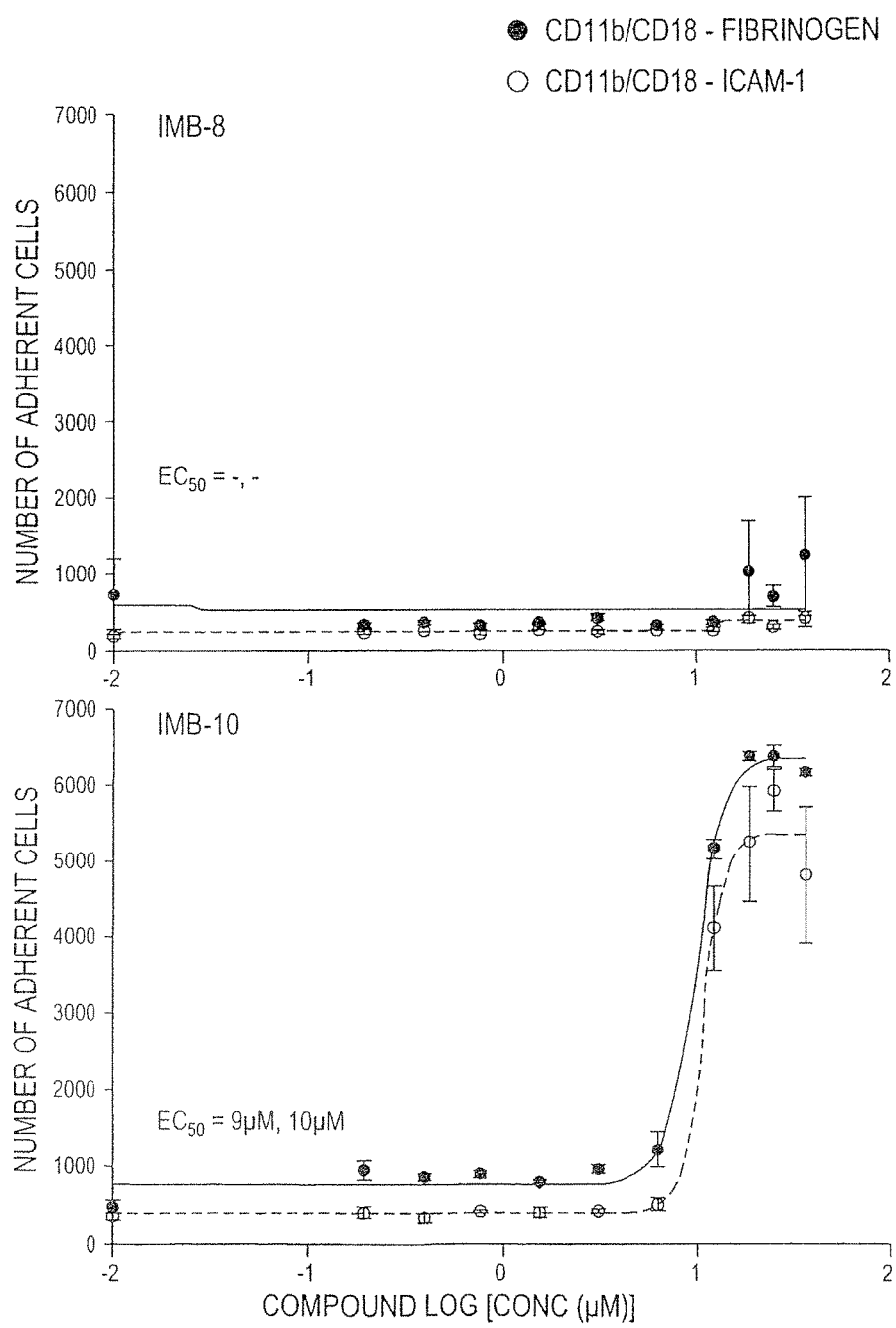
FIG. 6 shows dose-response curves depicting number of adherent cells in the presence of increasing amount of a small molecule. Adhesion of K562 CD11b+/CD18+ cells to the integrin CD11b/CD18 ligand fibrinogen or of K562 CD11a+/CD18+ cells to the integrin CD11a/CD18 ligand ICAM1 was measured in the presence of six different small molecules (IMB8, IMB10, 6, 8, 11 and 15). X-axis refers to the concentration of each small molecule used and y-axis shows the adherent cell number. Curve fitting was done using SIGMAPLOT to show a dose dependent increase of cell adhesion in the presence of a small molecule. Each dot represents mean+SEM of triplicate determinations from a representative experiment.
Figure 6:
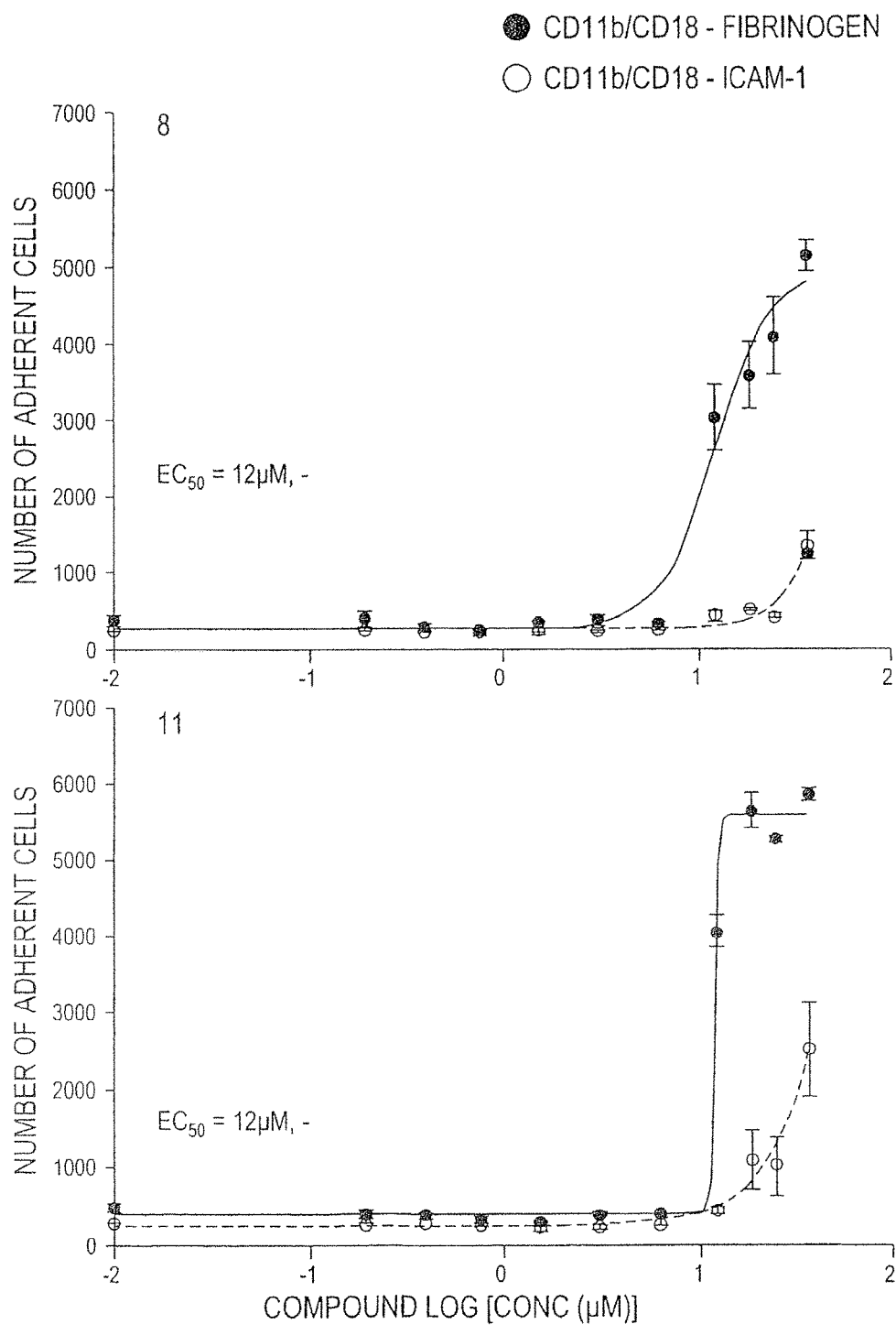
Figure 6:
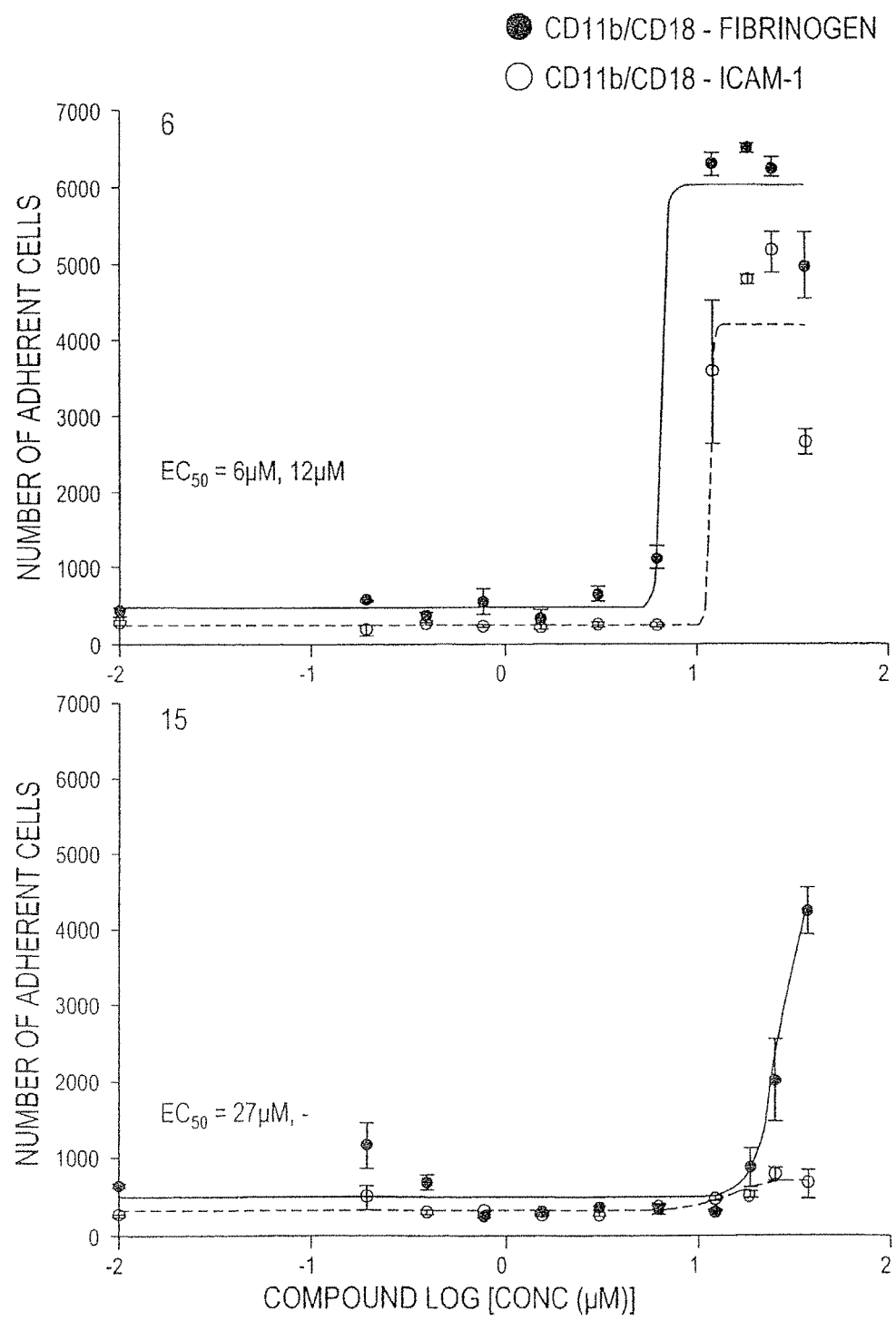

A subset of the newly discovered agonists were tested for their activity against integrins CD11b/CD18 and CD11a/CD18. The adhesion assays were performed in the presence of increasing amounts of each of the selected small molecules and the number of adherent cells under each condition was quantitated. The results, presented in FIG. 6, show that expectedly treatment with control compound IMB-8 showed no increase in cell adhesion for either of the two K562 cell lines (K562 cells stably expressing integrin CD11b/CD18 or K562 cells stably expressing integrin CD11a/CD18). However, IMB-10 increased equally well the adhesion of both CD11b/CD18 and CD11a/CD18 expressing K562 cells. Surprisingly, compounds 6, 8, 11 and 15 selectively increased adhesion of K562 cells stably expressing integrin CD11b/CD18 over K562 cells stably expressing integrin CD11a/CD18, suggesting that they may be selective agonists of the integrin CD11b/CD18 over integrin CD11a/CD18. The calculated EC50 value for each of the agonists is also shown in FIG. 6.

In Vivo Results

Coating Microtiter Plates with Ligand

Maxisorp microtiter plates (384-well) were coated with 1-20 g/mL fibrinogen (Fg), 4 g/mL iC3b or 0.375 g/mL ICAM1-Fc ligands in PBS++ overnight at 4° C.

Dose Response Curves

The following compounds were selected for measuring dose-response curves: 6, 8, 11 and 15. Additionally, IMB-8 and IMB-10 (from Björklund, M. et al., Biochemistry. 2006; 45:2862-2871) were used as controls. The selected small molecules were purchased from Actimol Timtec (Newark, Del.) and were each dissolved in DMSO at approximately 10 mg/mL and a dilution series was created.

For the adhesion assay in 384-well plates, the K562 cells were washed with TBS and cells (30,000/well) were transferred to the ligand-coated wells (Fg for CD11b/CD18 and ICAM1-Fc (R&D Systems, Minneapolis, Minn.) for CD11a/CD18) of microtiter plates in the assay buffer (TBS containing 1 mM each of Ca2+ and Mg2+ (TBS++). Compounds were transferred to each well and the assay plates were incubated at 37° C. in the presence of small molecule compounds and were incubated with small molecules for 30 min. In order to dislodge the non-adherent cell, the assay plates were gently inverted and kept in the inverted position for 20 min at room temperature. Adherent cells were quantified using either cell viability measuring reagents or automated imaging (see below).

In Vivo Inflammation Assays

The wild-type (WT) C57BL6 mice of approximately six weeks of age were purchased from Charles River Labs (Boston, Mass.). Mice were injected intraperitoneally with 1 mL of 4% w/v sterile thioglycolate (TG) (Sigma, St. Louis, MI) in PBS. Control mice were injected with PBS alone. Approximately five minutes after TG injection, 4 g each of compounds IMB-8, -6 or -11 were administered in 0.5 mL PBS through a tail vein injection. Twelve hours post-injection, the percentage of infiltrated neutrophils in the peritoneal lavage was determined using flow cytometry. Cells from the lavage fluid were labeled with FITC-labeled anti-mouse GR1 and PE-labeled anti-mouse CD11b antibodies (BD Pharmingen, Jan Jose, Calif.) and analyzed using FACS Calibur flow cytometer.

Figure 7:
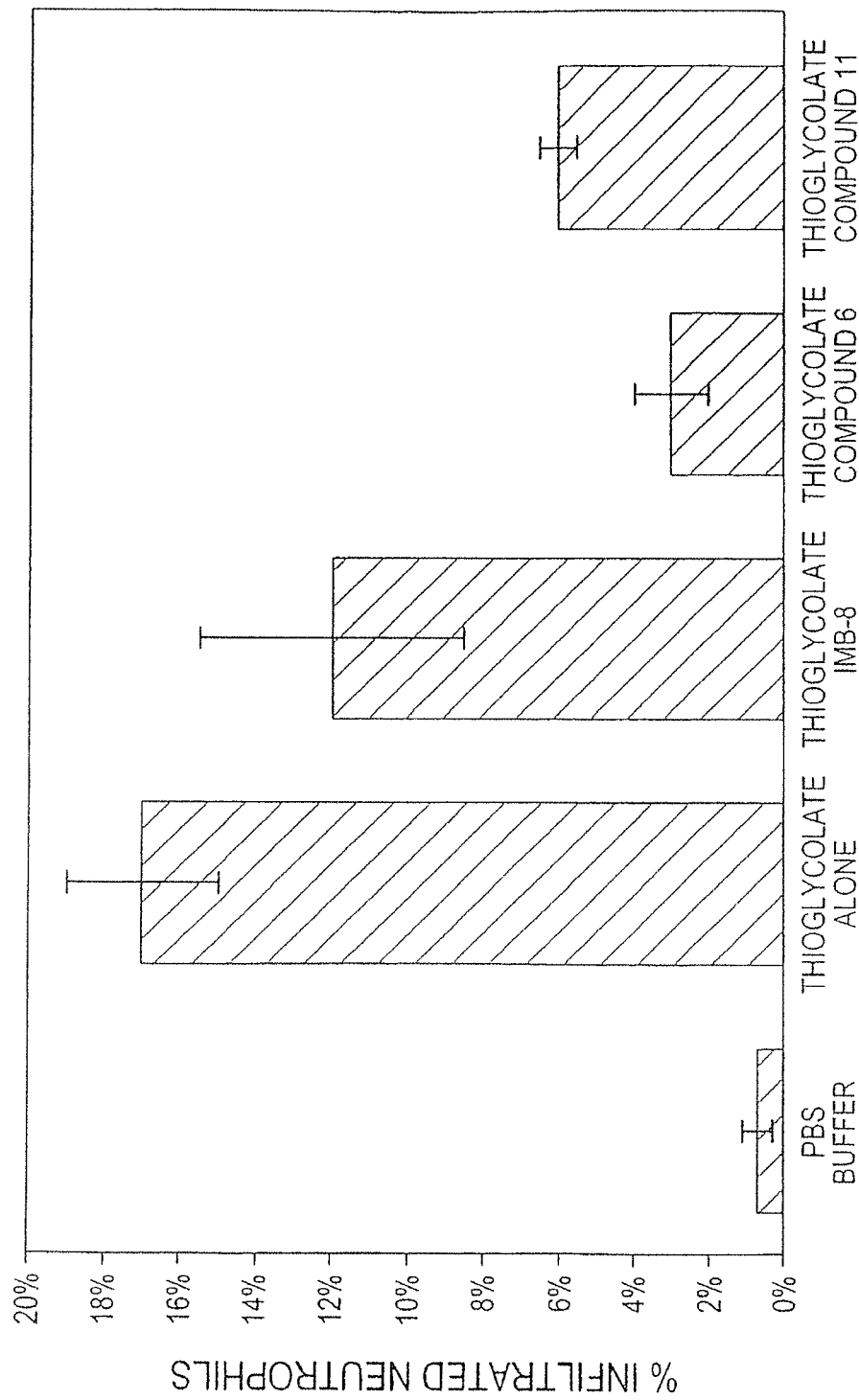
FIG. 7 shows that compounds 6 and 11 reduce leukocyte recruitment in vivo. Intraperitoneal thioglycolate injection was used to induce peritonitis in mice. PBS buffer alone was used as a control. Approximately five minutes after the thioglycolate injection, the test mice were administered IMB-8, compound 6 or compound 11 intravenously. Cells within the peritoneal cavity were collected after 12 h and counted using flow cytometry. The data shown are mean (SEM (n=3).

Reduction in Acute Inflammatory Response in Thioglycolate-induced Peritonitis Mouse Model Novel agonists show marked reduction in neutrophil influx into the peritoneum in a thioglycolate-induced inflammation mouse model of acute inflammation, as shown in FIG. 7. Injection of non-inflammatory solution of PBS buffer alone showed almost no neutrophil influx in the peritoneum. However, injection of a solution of 4% thioglycolate in PBS led to a massive influx of neutrophils (bar 2, FIG. 7). Administration of a control compound (IMB-8), which does not affect function of integrin CD11b/CD18 showed no change in the level of neutrophil influx due to TG injection. However, administration of either compound 6 or compound II (both integrin CD11b/CD18-selective agonists) showed a remarkable decrease in the number of neutrophils infiltrating to the mouse peritoneum due to TG injection.

All publications, patents and patent applications are herein incorporated by reference in their entirety to the same extent as if each individual publication, patent or patent application was specifically and individually indicated to be incorporated by reference in its entirety.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:
1. A no-wash, cell-based assay for the identification of small molecule modulators of integrin CD11b/CD18, the assay consisting of:
   contacting cells with a solution comprising a test compound on a substrate treated with a compound that affects cell adhesion;

inverting the substrate such that non-adherent cells move away from the substrate by the action of gravity;

removing the solution from the substrate after inverting the substrate without contacting the substrate with an additional liquid to wash or rinse the substrate; and detecting adherent cells on the substrate, wherein detecting adherent cells comprises measuring the viability of the adherent cells or imaging the adherent cells.

2. The no-wash, cell-based assay of claim 1, wherein the cells are K562 cells expressing integrin CD11b/CD18.

3. The no-wash, cell-based assay of claim 1, wherein the compound that affects cell adhesion promotes cell adhesion to the substrate.

4. The no-wash, cell-based assay of claim 3, wherein the compound that affects cell adhesion is selected from the group consisting of fibrinogen, iCb3, factor X, ICAM-1, NIF, and denatured BSA.

5. The no-wash, cell-based assay of claim 3, wherein the solution further comprises $Mg^{2+}$, $Ca^{2+}$, or a mixture thereof.

6. The no-wash, cell-based assay of claim 1, wherein the solution is removed from the substrate by aspirating the solution.

7. The no-wash, cell-adhesion-based assay of claim 1, wherein the cells are treated with a fixative prior to removing the solution from the substrate.

8. The no-wash, cell-adhesion-based assay of claim 7, wherein the fixative is formaldehyde.

9. A no-wash, cell-adhesion-based assay for the identification of small molecule modulators of integrin CD11b/CD18, the assay consisting of:

contacting cells with a solution comprising a test compound on a substrate treated with a compound that affects cell adhesion;

inverting the substrate such that non-adherent cells move away from the substrate by the action of gravity without contacting the substrate with an additional liquid to wash or rinse the substrate;

and detecting adherent cells on the substrate.

10. The no-wash, cell-adhesion-based assay of claim 9, wherein the cells are K562 cells expressing integrin CD11b/CD18.

11. The no-wash, cell-adhesion-based assay of claim 9, wherein the compound that affects cell adhesion promotes cell adhesion to the substrate.

12. The no-wash, cell-adhesion-based assay of claim 11, wherein the compound that affects cell adhesion is selected from the group consisting of fibrinogen, iCb3, factor X, ICAM-1, NIF, and denatured BSA.

13. The no-wash, cell-adhesion-based assay of claim 11, wherein the solution further comprises $Mg^{2+}$, $Ca^{2+}$, or a mixture thereof.

14. The no-wash, cell-adhesion-based assay of claim 9, wherein detecting adherent cells comprises measuring the viability of the adherent cells or imaging the adherent cells.

* * * * *